(12) United States Patent
Gellman et al.

(10) Patent No.: US 7,232,447 B2
(45) Date of Patent: Jun. 19, 2007

(54) SUTURING INSTRUMENT WITH DEFLECTABLE HEAD

(75) Inventors: Barry N. Gellman, N. Easton, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 433 days.

(21) Appl. No.: 10/460,140

(22) Filed: Jun. 12, 2003

(65) Prior Publication Data

US 2003/0233104 A1    Dec. 18, 2003

Related U.S. Application Data

(60) Provisional application No. 60/388,458, filed on Jun. 12, 2002.

(51) Int. Cl.
*A61B 17/04* (2006.01)
*A61B 17/12* (2006.01)

(52) U.S. Cl. .................................................. 606/144

(58) Field of Classification Search ............... 606/139, 606/144, 147, 148, 149
See application file for complete search history.

(56) References Cited

U.S. PATENT DOCUMENTS

| | | |
|---|---|---|
| 342,773 A | 6/1886 | Bailey |
| 919,138 A | 4/1909 | Drake et al. |
| 1,037,864 A | 9/1912 | Carlson et al. |
| 1,449,087 A | 3/1923 | Bugbee |
| 1,815,725 A | 7/1931 | Pilling et al. |
| 1,822,330 A | 9/1931 | Ainslie |
| 2,577,240 A | 12/1951 | Findley |
| 2,579,192 A | 12/1951 | Kohl |
| 3,013,559 A | 12/1961 | Thomas |
| 3,160,157 A | 12/1964 | Chisman |

(Continued)

FOREIGN PATENT DOCUMENTS

EP    0 140 557    5/1985

(Continued)

OTHER PUBLICATIONS

Lecture "Human Gross Anatomy and Embryology Pelvic Organs and Pelvic Diaphragm" by Dr. Roberts, University of Minnesota Medical School. Lecture given Fall 2000. Information posted tot he internet before Oct. 17, 2000. Describes pelvic floor area.

(Continued)

*Primary Examiner*—Michael J. Hayes
*Assistant Examiner*—M. Thomas Andersen
(74) *Attorney, Agent, or Firm*—Robert J. Tosti; Steven M. Jensen; Edwards Angell Palmer & Dodge LLP

(57) ABSTRACT

Suturing instruments in accordance with the invention are dimensioned and configured to apply sutures to approximate, ligate, or fixate tissue in, for example, open, mini-incision, trans-vaginal, laparoscopic, or endoscopic surgical procedures. In some embodiments, the suturing instruments include a distal portion that is deflectably and/or pivotally coupled to the remainder of the instrument for improved maneuverability and functionality during surgery. In other embodiments, the suturing instruments are capable of housing multiple needle and suture assemblies and/or reloading the needle and suture assembly without removing the instrument from the surgical site.

6 Claims, 30 Drawing Sheets

U.S. PATENT DOCUMENTS

| | | | |
|---|---|---|---|
| 3,470,875 A | 10/1969 | Johnson | |
| 3,557,780 A * | 1/1971 | Sato | 600/141 |
| 3,638,653 A | 2/1972 | Berry | |
| 3,840,017 A | 10/1974 | Violante | |
| 3,918,455 A | 11/1975 | Coplan | |
| 3,946,740 A | 3/1976 | Bassett | |
| 3,986,468 A | 10/1976 | Szostak et al. | |
| 4,161,951 A | 7/1979 | Scanlan, Jr. | |
| 4,164,225 A | 8/1979 | Johnson et al. | |
| 4,224,947 A | 9/1980 | Fukuda | |
| 4,235,177 A | 11/1980 | Arbuckle | |
| 4,235,238 A | 11/1980 | Ogiu et al. | |
| 4,236,470 A | 12/1980 | Stenson | |
| 4,312,337 A | 1/1982 | Donhue | |
| 4,345,601 A | 8/1982 | Fukuda | |
| 4,493,323 A | 1/1985 | Albright et al. | |
| 4,548,202 A | 10/1985 | Duncan | |
| 4,557,265 A | 12/1985 | Andersson | |
| 4,579,072 A | 4/1986 | Koike et al. | |
| 4,596,249 A | 6/1986 | Freda et al. | |
| 4,602,635 A | 7/1986 | Mulhollan et al. | |
| 4,621,640 A | 11/1986 | Mulhollan et al. | |
| 4,635,638 A | 1/1987 | Weintraub et al. | |
| 4,762,260 A | 8/1988 | Richards et al. | |
| 4,781,190 A | 11/1988 | Lee | |
| 4,890,615 A | 1/1990 | Caspari et al. | |
| 4,898,155 A | 2/1990 | Ovil et al. | |
| 4,899,746 A | 2/1990 | Brunk | |
| 4,923,461 A | 5/1990 | Caspari et al. | |
| 4,926,860 A | 5/1990 | Stice et al. | |
| 4,935,027 A | 6/1990 | Yoon | |
| 4,957,498 A | 9/1990 | Caspari et al. | |
| 5,037,433 A | 8/1991 | Wilk et al. | |
| 5,042,707 A * | 8/1991 | Taheri | 606/213 |
| 5,047,039 A | 9/1991 | Avant et al. | |
| 5,067,957 A | 11/1991 | Jervis | |
| 5,100,415 A | 3/1992 | Hayhurst | |
| 5,100,418 A | 3/1992 | Yoon et al. | |
| 5,100,421 A | 3/1992 | Christoudias | |
| 5,100,498 A | 3/1992 | Takeuchi et al. | |
| 5,188,636 A | 2/1993 | Fedotov | |
| 5,258,011 A | 11/1993 | Drews | |
| 5,281,237 A | 1/1994 | Gimpelson | |
| 5,306,281 A | 4/1994 | Beurrier | |
| 5,308,353 A | 5/1994 | Beurrier | |
| 5,324,298 A | 6/1994 | Phillips et al. | |
| 5,336,231 A | 8/1994 | Adair | |
| 5,364,408 A | 11/1994 | Gordon | |
| 5,387,221 A | 2/1995 | Bisgaard | |
| 5,389,103 A | 2/1995 | Melzer et al. | |
| 5,391,174 A | 2/1995 | Weston | |
| 5,417,699 A | 5/1995 | Klein et al. | |
| 5,417,700 A | 5/1995 | Egan | |
| 5,454,823 A | 10/1995 | Richardson et al. | |
| 5,458,609 A | 10/1995 | Gordon et al. | |
| 5,522,820 A * | 6/1996 | Caspari et al. | 606/144 |
| 5,527,321 A | 6/1996 | Hinchliffe | |
| 5,540,704 A | 7/1996 | Gordon et al. | |
| 5,540,705 A | 7/1996 | Meade et al. | |
| 5,549,617 A * | 8/1996 | Green et al. | 606/144 |
| 5,549,637 A * | 8/1996 | Crainich | 606/207 |
| 5,562,686 A | 10/1996 | Sauer et al. | |
| 5,573,542 A | 11/1996 | Stevens | |
| 5,575,800 A | 11/1996 | Gordon | |
| 5,578,044 A | 11/1996 | Gordon et al. | |
| 5,591,179 A | 1/1997 | Edelstein | |
| 5,593,421 A | 1/1997 | Bauer | |
| 5,662,664 A | 9/1997 | Gordon et al. | |
| 5,662,666 A | 9/1997 | Onuki et al. | |
| 5,665,096 A | 9/1997 | Yoon | |
| 5,690,653 A | 11/1997 | Richardson et al. | |
| 5,700,272 A | 12/1997 | Gordon et al. | |
| 5,700,273 A | 12/1997 | Buelna et al. | |
| 5,713,910 A | 2/1998 | Gordon et al. | |
| 5,741,277 A | 4/1998 | Gordon et al. | |
| 5,741,279 A | 4/1998 | Gordon et al. | |
| 5,755,727 A | 5/1998 | Kontos | |
| 5,759,188 A | 6/1998 | Yoon | |
| 5,779,718 A | 7/1998 | Green et al. | |
| 5,782,845 A | 7/1998 | Shewchuk | |
| 5,827,298 A | 10/1998 | Hart et al. | |
| 5,843,001 A | 12/1998 | Goldenberg | |
| 5,855,585 A | 1/1999 | Kontos | |
| 5,860,992 A | 1/1999 | Daniel et al. | |
| 5,899,909 A | 5/1999 | Claren et al. | |
| 5,904,692 A | 5/1999 | Steckel et al. | |
| 5,908,428 A | 6/1999 | Scirica et al. | |
| 5,911,727 A | 6/1999 | Taylor | |
| 5,919,199 A | 7/1999 | Mers Kelly et al. | |
| 5,954,732 A | 9/1999 | Hart et al. | |
| 6,048,351 A | 4/2000 | Gordon et al. | |
| 6,051,006 A | 4/2000 | Shluzas et al. | |
| 6,117,067 A | 9/2000 | Gil-Vernet | |
| 6,224,525 B1 | 5/2001 | Stein | |
| 6,443,962 B1 | 9/2002 | Gaber | |
| 6,454,778 B2 | 9/2002 | Kortenbach | |
| 6,743,239 B1 * | 6/2004 | Kuehn et al. | 606/139 |

FOREIGN PATENT DOCUMENTS

| | | |
|---|---|---|
| EP | 0 589 409 | 3/1994 |
| EP | 0 674 875 | 10/1995 |
| GB | 2 268 690 | 1/1994 |
| WO | WO/90/03766 | 4/1990 |
| WO | WO 92/12674 | 8/1992 |
| WO | 99/47050 | 2/1993 |
| WO | WO/93/01750 | 2/1993 |
| WO | WO 94/05213 | 3/1994 |
| WO | WO/94/13211 | 6/1994 |
| WO | 96/09796 | 4/1996 |
| WO | WO 96/09796 | 4/1996 |
| WO | WO 96/27331 | 9/1996 |
| WO | 01/28432 | 4/2001 |

OTHER PUBLICATIONS

GyneFlex™—Instructions : Female Pelvic Floor Muscles. Shows color diagrams of the pelvic floor area. Printed Feb. 7, 2003.

"Physicaians/Plastic Surgery/Pelvic Floor Dysfunction", Abington Memorial Hospital. Printed Feb. 6, 2003. Describe what the pelvic area constitutes.

International Search Report for International Application No. PCT/US03/18486, dated Jan. 27, 2004.

* cited by examiner

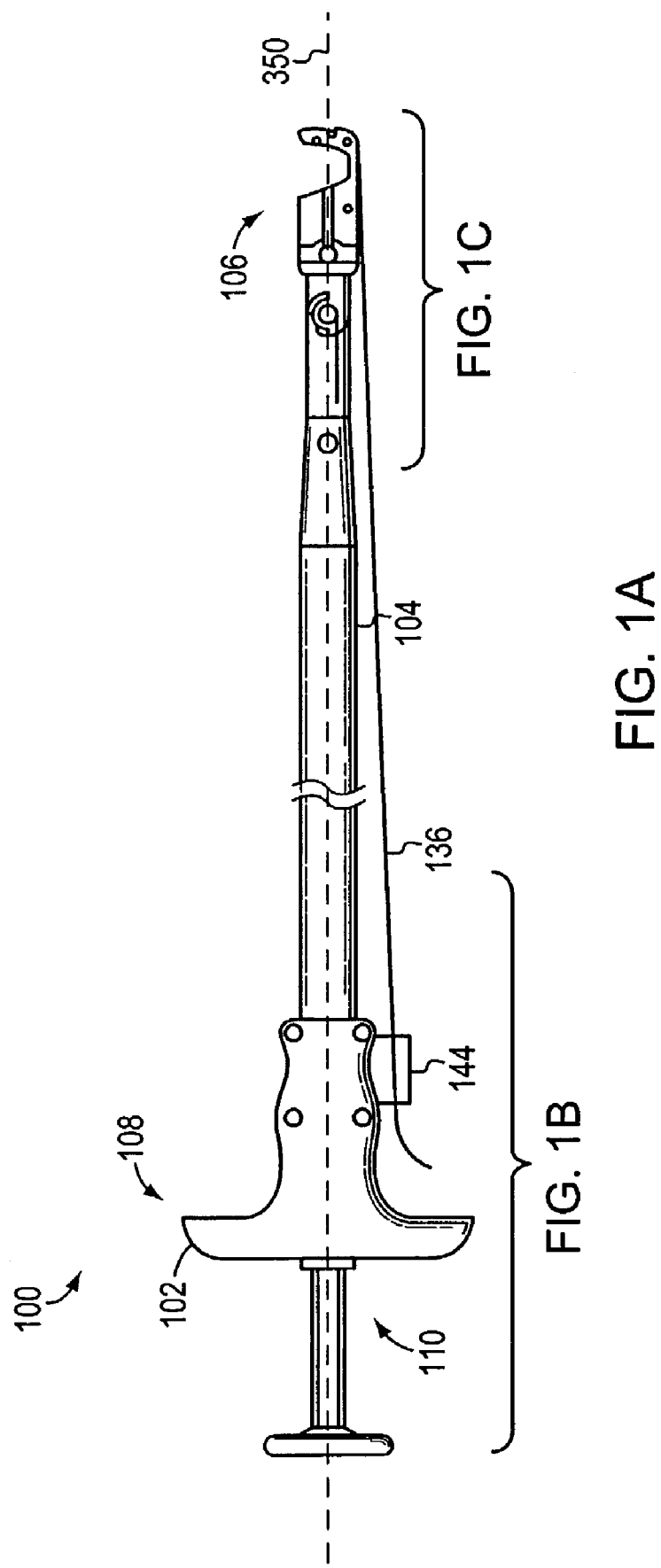

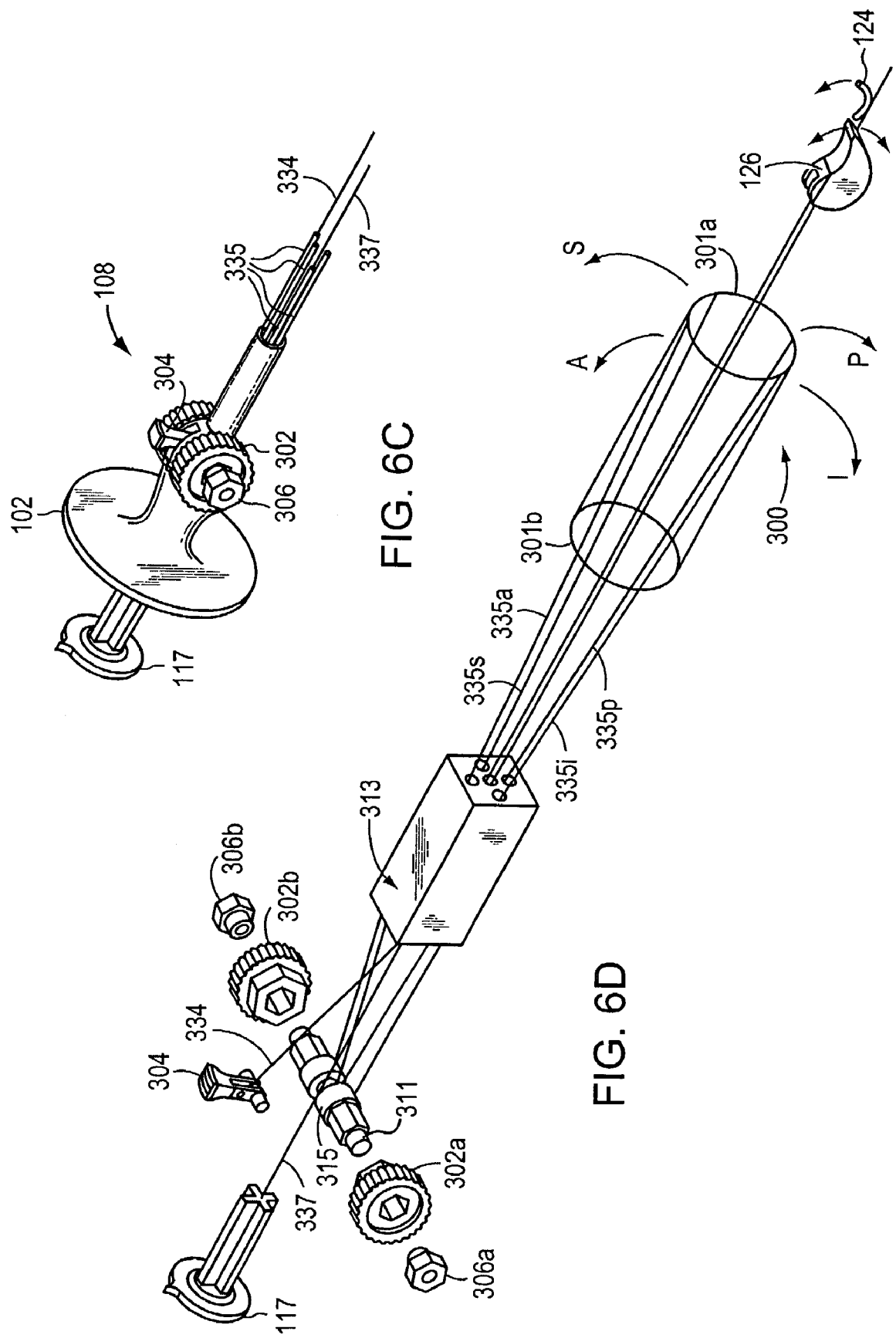

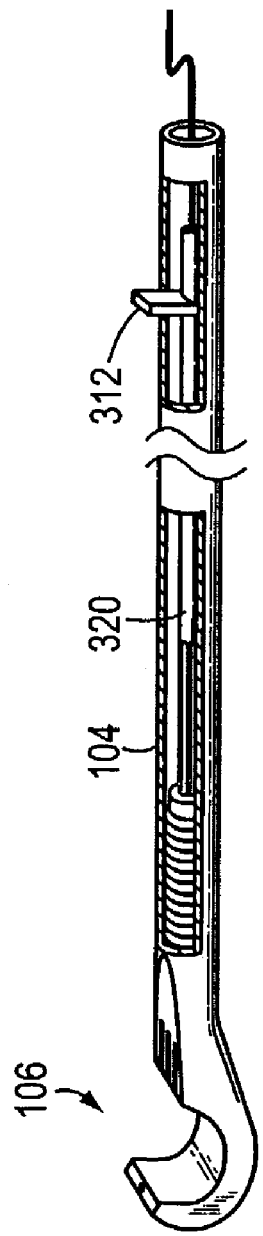
FIG. 6I
FIG. 6J
FIG. 6K

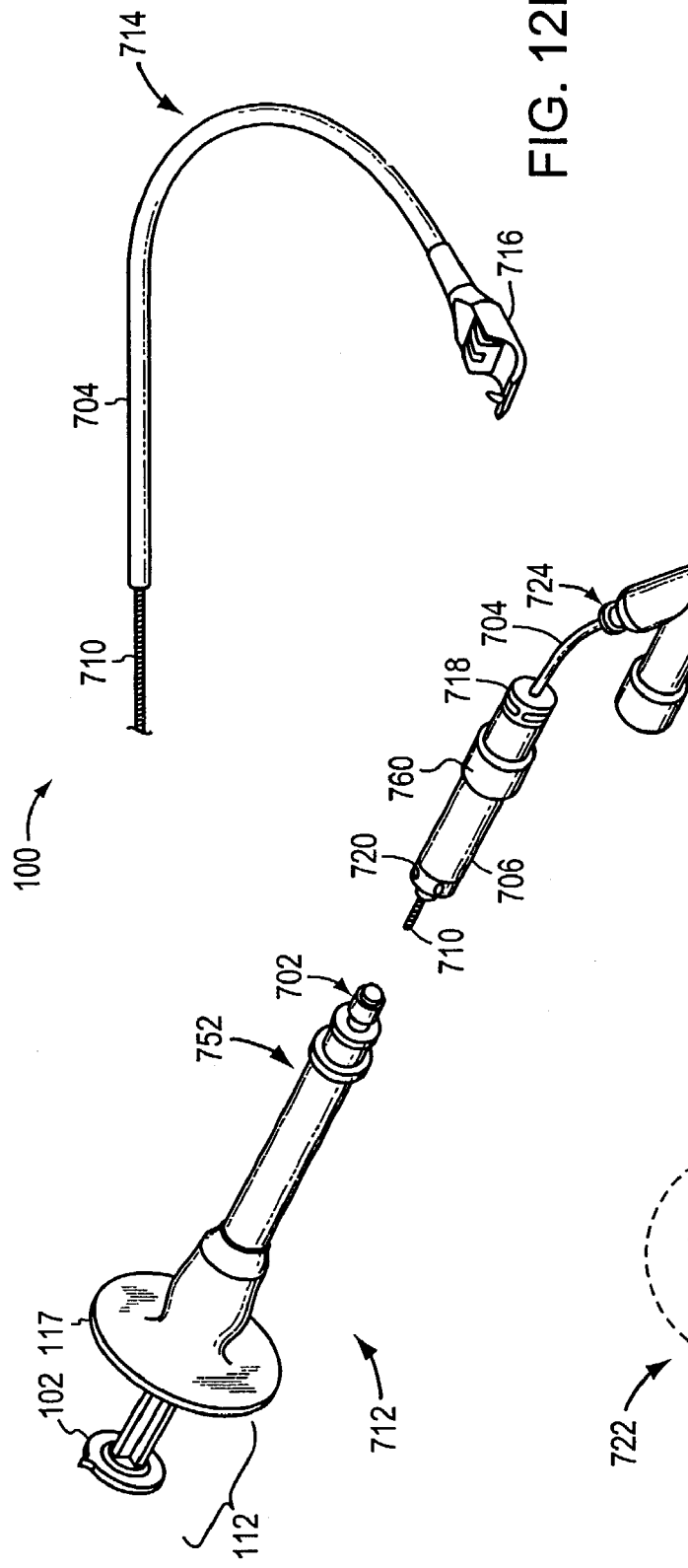
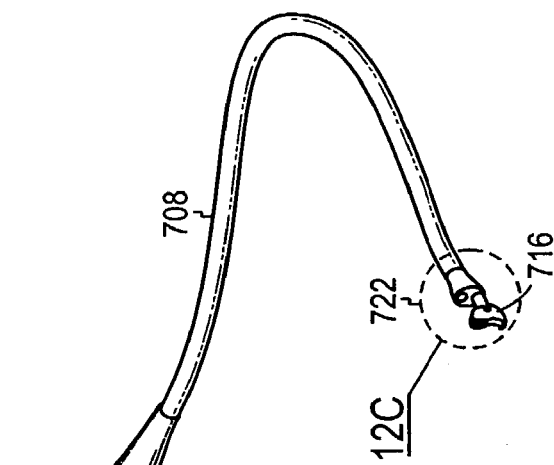
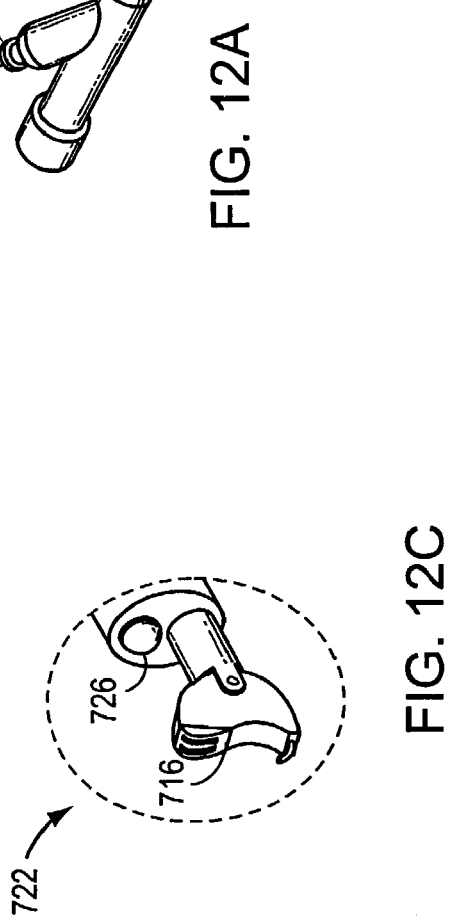
FIG. 12A
FIG. 12B
FIG. 12C

SUTURING INSTRUMENT WITH DEFLECTABLE HEAD

CROSS-REFERENCE TO RELATED APPLICATION

This application incorporates by reference, and claims priority to and the benefit of, provisional U.S. Patent Application Ser. No. 60/388,458, which was filed on Jun. 12, 2002.

TECHNICAL FIELD

The invention relates to medical devices and, more specifically, to devices for approximation, ligation, or fixation of tissue using sutures.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. Furthermore, many of the instruments are complicated and expensive to use due to the numerous parts and/or subassemblies required to make them function properly.

Suturing instruments, and more specifically suturing instruments used in endoscopic procedures, are generally rigid and do not provide the operator a range of motion to access difficult to reach parts of the anatomical region requiring sutures. Accordingly, multiple instruments of various configurations and sizes must be used to access all of the necessary tissue areas. These limitations of suturing instruments complicate the endoscopic procedure for the surgeon by requiring the insertion and removal of multiple instruments from a surgical site as the target suturing area changes during the course of the surgical procedure.

Many medical procedures require that multiple sutures be placed within a patient. Typical suturing instruments enable a surgeon to place only one suture at a time. With such suturing instruments, the surgeon is required to remove the instrument from a surgical site and reload the instrument between placing each suture. Further, the surgeon may be required to use forceps or other instruments to help place the suture. In some instances, the forceps or other instruments may require an additional incision to access the surgical site.

Thus, suturing remains a delicate and time-consuming aspect of most surgeries, including those performed endoscopically. Accordingly, there is an unresolved need in the art to provide a suturing instrument with improved maneuverability, efficiency, and functionality during a surgical procedure.

SUMMARY OF THE INVENTION

The invention generally relates to surgical instruments for performing a surgical procedure, such as placing one or more sutures through tissue. The suturing instruments disclosed herein are dimensioned and configured to apply sutures to approximate, ligate, or fixate tissues in, for example, open, mini-incision, trans-vaginal, laparoscopic, or endoscopic surgical procedures.

More particularly, in some embodiments, the invention is directed to suturing instruments that include a distal portion that is deflectably and/or pivotally coupled to the remainder of the instrument for improved maneuverability and functionality during surgery.

In other embodiments the invention is directed to suturing instruments capable of housing multiple needle and suture assemblies and/or reloading the needle and suture assembly without removing the instrument from the surgical site. Such suturing instruments allow a surgeon to place multiple sutures without having to reload the instrument after each suture is placed, which is more efficient and less invasive than a procedure where the surgeon has to remove the instrument from the surgical site to reload. This is particularly helpful when the surgical site is located deep within a body and not easily repeatably accessible.

In general, in a first aspect, the invention features a suturing instrument that includes an elongate body member having a middle portion and a distal portion. The distal portion extends distally from the middle portion and is deflectable at a predetermined angle relative to the middle portion. The predetermined angle of deflection of the distal portion may range from about −90° to about 90°. The suturing instrument also includes a needle deployment mechanism disposed at least partially within the elongate body member. The needle deployment mechanism is connectable to a needle for moving the needle out of the distal portion of the elongate body member.

In one embodiment according to the first aspect of the invention, the elongate member also includes at least one tension member that is slidably disposed at least partially in the elongate member and is connected to its distal portion. In this embodiment, the suturing instrument may include at least one deflection control member coupled to the tension member and disposed opposite the distal portion of the elongate body member for controlling deflection of the distal portion.

In another embodiment according to the first aspect of the invention, the distal portion is pivotable about a first axis that is perpendicular to the longitudinal axis of the elongate body member. In this embodiment, the suturing instrument may include a first pivot control lever disposed opposite the distal portion of the elongate body member, and a pivot wire rotatably disposed in the elongate body member and coupled to the distal portion. The first pivot control lever may be coupled to the pivot wire for controlling pivoting of the distal portion.

In yet another embodiment according to the first aspect of the invention, the distal portion includes a first beveled surface for contacting the middle portion and the middle portion includes a second beveled surface for contacting the distal portion. According to one feature of this embodiment, a first angle defined by the first beveled surface and a second angle defined the second beveled surface are substantially equal. The sum of the angles may substantially equal 90°. According to another feature, the elongate body member includes a first resilient member for biasing the distal portion towards the middle portion along a longitudinal axis of the elongate member. The suturing instrument of this embodiment may also include a deflection control mechanism coupled to the distal portion for deflecting the distal portion at the predetermined angle relative to the middle portion by rotating the distal portion about a longitudinal axis of the elongate body member.

In still another embodiment according to the first aspect of the invention, the elongate body member includes a locking mechanism for securing the distal portion at the predetermined angle relative to the middle portion. The locking mechanism may include a first plurality of teeth disposed on the first beveled surface and a second plurality of teeth disposed on the second beveled surface that are configured to mesh with the first plurality of teeth. Alternatively, the locking mechanism may include a plurality of detents that are defined by the first beveled surface and are circumferentially disposed about the first beveled surface; and a ball disposed in the second beveled surface and dimensioned to fit at least one of the plurality of detents. In this feature, the second beveled surface may define an aperture for receiving the ball therein. Also, a second resilient member may be disposed in the aperture for biasing the ball into engagement with the at least one of the plurality of detents.

In yet another embodiment according to the first aspect of the invention, the needle deployment mechanism includes a needle carrier that is disposed at least partially within the distal portion of the elongate body member and is slidably movable out of the distal portion. The needle deployment mechanism optionally includes an actuator coupled to the needle carrier and disposed opposite the distal portion. The actuator may be at least partially housed by a handle disposed opposite the distal portion.

The invention is also related generally to a method for placing sutures in tissue. The method includes the step of providing a suturing instrument having an elongate body member that includes a middle portion and a distal portion extending distally from the middle portion and deflectable at a predetermined angle relative to the middle portion; and a needle deployment mechanism disposed at least partially within the elongate body member and connectable to a needle for moving the needle out of the distal portion. The method further includes the steps of disposing a needle within the distal portion; disposing the suturing instrument in a body; deflecting the distal portion of the suturing instrument thereby positioning the distal portion proximal to the tissue; and actuating the needle deployment mechanism thereby moving the needle out of the distal portion and through the tissue.

In general, in a second aspect, the invention features a suturing instrument that includes an elongate body member having a longitudinal axis. The elongate body member has a distal portion that is pivotable about at least one axis that is substantially perpendicular to the longitudinal axis of the elongate body member. The suturing instrument also includes a needle deployment mechanism disposed at least partially within the elongate body member. The needle deployment mechanism is connectable to a needle for moving the needle out of the distal portion. Also, the elongate body member may include a handle disposed opposite the distal portion.

In one embodiment according to the second aspect of the invention, the suturing instrument also includes a pivot control lever disposed opposite the distal portion of the elongate body member for controlling pivoting of the distal portion. In a first version of this embodiment, the suturing instrument includes a pivot mechanism disposed in the elongate body member and coupled to the distal portion. The pivot control lever may be coupled to the pivot mechanism for controlling pivoting of the distal portion. In a second version of this embodiment, the elongate body member may include an inner portion coupled to the distal portion, and an outer portion coupled to the pivot control lever and slidably disposed at least partially along the inner portion. According to one feature, the suturing instrument also has a linkage coupled to the outer portion and the distal portion. The linkage is configured to cause the distal portion to pivot about the first axis when the outer portion is displaced relative to the inner portion. According to another feature, the suturing instrument also includes a resilient member for biasing the outer portion towards the proximal portion of the elongate body member.

Further, in various features of the needle deployment mechanism of this embodiment of the suturing instrument, the needle deployment mechanism includes a needle carrier that is disposed at least partially within the distal portion of the elongate body member and is slidably movable out of the distal portion.

According to one particular feature of the second version of this embodiment, the needle deployment mechanism also has a resilient loop of material disposed at least partially within the elongate body member and coupled to the needle carrier. The needle deployment mechanism also includes an actuator that is coupled to the needle carrier via the resilient loop of material to move the needle carrier of the distal portion. The actuator may be at least partially housed by the handle.

According to another feature, the needle deployment mechanism also includes a needle carrier control rod that is slidably disposed at least partially within the elongate body member and coupled to the needle carrier. The needle carrier control rod may optionally be made of a superelastic material, such as a nickel-titanium alloy. The needle carrier control rod is configured to move the needle carrier when the needle carrier control rod is slidably advanced. The needle deployment mechanism may include an actuator coupled to the needle carrier control rod to advance the needle carrier control rod. The actuator is disposed opposite the distal portion of the elongate member, for example, at least partially housed by the handle.

According to yet another feature of the second version of this embodiment, the needle deployment mechanism also includes a camshaft disposed within the distal portion of the elongate body member and coupled to the needle carrier and a drum rotatably disposed within the distal portion of the elongate body member and coupled to the camshaft for moving the camshaft when the drum rotates. The needle deployment mechanism according to this feature further includes a push wire slidably disposed within the elongate body member and having a distal end coupled to the drum for causing the drum to rotate. The needle deployment mechanism may also include an actuator coupled to a proximal end of the push wire for advancing the push wire. The actuator is disposed opposite the distal portion of the elongate member, for example, at least partially housed by the handle.

In another embodiment according to the second aspect of the invention, the distal portion of the suturing instrument includes a first gear that is rotatable about a first axis substantially perpendicular to the longitudinal axis of the elongate body member. According to one feature of this embodiment, a middle portion of the elongate body member includes a second gear rotatable about the longitudinal axis and meshed with the first gear. According to this feature, the distal portion pivots about the first axis when the second gear rotates about the longitudinal axis. Optionally, the suturing instrument includes a pivot control mechanism disposed at least partially within the middle portion and coupled to the second gear for causing the second gear to rotate about the longitudinal axis, a pivot control lever disposed opposite the distal portion of the elongate body member and coupled to the pivot control mechanism for controlling pivoting of the distal portion.

In yet another embodiment according to the second aspect of the invention, the distal portion is rotatable about the longitudinal axis of the elongate body member. In this embodiment, the suturing instrument may include a rotation control mechanism disposed opposite the distal portion of the elongate body member, and a rotation rod rotatably disposed in the elongate body member and coupled to the distal portion. The rotation control mechanism may be coupled to the rotation rod for controlling rotation of the distal portion.

In general, in a third aspect, the invention features a suturing instrument for use with an endoscope. The suturing instrument according to this aspect of the invention includes an elongate body member having a flexible tubular member and a distal portion attached to a distal end of the flexible tubular member. The flexible tubular member is dimensioned to slidably and rotationally fit within a working channel of an endoscope. The suturing instrument according to this aspect of the invention also includes a needle deployment mechanism disposed at least partially within the elongate body member and connectable to a needle for moving the needle out of the distal portion.

In one embodiment according to the third aspect of the invention, the needle deployment mechanism includes a needle carrier that is disposed at least partially within the distal portion of the elongate body member and is slidably movable out of the distal portion; a carrier drive wire slidably disposed within a lumen defined by the flexible tubular member and coupled to the needle carrier; and an actuator coupled to the carrier drive wire. According to one feature of this embodiment, the elongate body member may include a proximal portion including a handle at least partially housing the actuator. The tubular member may be releasably attached to the proximal portion. Optionally, the distal portion is rotatable about a longitudinal axis of the elongate body member relative to the proximal portion. The suturing instrument may also include a rotation control mechanism disposed in the proximal portion of the elongate body member for controlling rotation of the distal portion. Also, according to this feature, the proximal portion includes a carrier drive wire socket releasably coupled to the proximal portion for receiving the carrier drive wire. The proximal portion may also include a locking socket that is rotationally and releasably coupled to the carrier drive wire socket and serves to secure a proximal end of the tubular member. Further, the proximal portion may also include a scope adapter for securing the proximal portion to the working channel of the endoscope.

In another embodiment according to the third aspect of the invention, the distal portion of the elongate body member is pivotable about a first axis, which is substantially perpendicular to a longitudinal axis of the elongate body member.

Also, the invention features a method for placing sutures in tissue. The method includes the step of providing an endoscope defining a working channel through. The working channel of the endoscope has an opening at a distal end of the endoscope. The method further includes the step of providing a suturing instrument that includes an elongate body member having a flexible tubular member with a distal end and a proximal end; the flexible tubular member dimensioned to slidably and rotationally fit within the working channel of the endoscope, and a distal portion attached to the distal end of the flexible tubular member. The suturing instrument also includes a needle deployment mechanism disposed at least partially within the elongate body member and connectable to a needle for moving the needle out of the distal portion. The method also includes the steps of inserting the proximal end of the flexible tubular member into the opening; passing the flexible tubular member through the working channel of the endoscope, disposing a needle within the distal portion, disposing the endoscope within a body, positioning the distal portion proximal to the tissue, and actuating the needle deployment mechanism thereby moving the needle out of the distal portion and through the tissue.

In various embodiments according to the foregoing aspects of the invention, the suturing instrument includes a needle disposed within the distal portion. Also, the distal portion of the suturing instrument of claim may include a needle catch configured to receive a needle, the needle catch defining a retention slot including at least two flexible edges.

In general, in a fourth aspect, the invention features a suturing instrument that includes an elongate body member having a distal portion. The distal portion includes a needle catch defining an aperture. The suturing instrument according to this aspect of the invention includes a needle deployment mechanism disposed at least partially within the elongate body member for moving a needle out of the distal portion and to the needle catch as well as a needle reloading mechanism disposed at least partially within the elongate body member for pushing the needle into the aperture of the needle catch. The needle catch is optionally slidably movable along a longitudinal axis of the elongate body member.

In one embodiment according to the fourth aspect of the invention, the needle deployment mechanism includes a needle carrier that is disposed at least partially within the distal portion of the elongate body member and is slidably movable out of the distal portion. The needle deployment mechanism also includes an actuator that is coupled to the needle carrier and disposed opposite the distal portion of the elongate body member. The needle carrier has a distal end that, optionally, defines a lumen for receiving the needle therein.

In another embodiment according to the fourth aspect of the invention, the needle reloading mechanism includes a pusher rod and a rod actuator for moving the pusher rod towards the distal portion of the elongate body member. According to one feature of this embodiment, the rod actuator is disposed opposite the distal portion of the elongate body member substantially perpendicularly to the pusher rod. According to another feature, the pusher rod comprises a substantially concave distal end. Also, according to yet another feature, the needle reloading mechanism has a hook coupled to a resilient member for biasing the pusher rod away from the distal portion of the elongate body member.

In still another embodiment according to the fourth aspect of the invention, the needle catch defines a retention slot including at least two flexible edges for retaining the needle therein, the retention slot in communication with the aperture. At least one of the flexible edges may have at least one protrusion extending into the retention slot. According to another feature of this embodiment, the suturing instrument includes a needle disposed within the distal portion. The needle has a suture attached thereto and is releasable from the needle catch by pulling on the free end of the suture after the needle reloading mechanism pushes the needle into the aperture.

In yet another embodiment according to the fourth aspect of the invention, the suturing instrument also includes a handle disposed opposite the distal portion of the elongate body member, which at least partially houses the needle deployment mechanism and the needle reloading mechanism.

In general, in a fifth aspect, the invention features a suturing instrument that includes an elongate body member having a distal portion. The distal portion includes a first operative portion and a second operative portion. The suturing instrument also includes a needle deployment mechanism that is disposed at least partially within the elongate body member and includes a first needle carrier disposed at least partially within the first operative portion and connectable to a first needle for moving the first needle out of the first operative portion, and a second needle carrier disposed at least partially within the second operative portion and connectable to a second needle for moving the second needle out of the second operative portion.

In a first embodiment according to the fifth aspect of the invention, the suturing instrument includes a handle that is disposed opposite the distal portion of the elongate body member and at least partially houses the needle deployment mechanism.

In a second embodiment according to the fifth aspect of the invention, the first operative portion and the second operative portion of the distal portion form a unitary operative portion.

In a third embodiment according to the fifth aspect of the invention, the suturing instrument includes an actuator coupled to the first needle carrier and the second needle carrier and disposed opposite the distal portion of the elongate body member. According to one feature of this embodiment, the actuator includes a first sub-actuator coupled to the first needle carrier and a second sub-actuator coupled to the second needle carrier. The first needle carrier and the second needle carrier are actuatable either sequentially or simultaneously.

In a fourth embodiment according to the fifth aspect of the invention, the suturing instrument includes a first needle disposed within the first operative portion, and a second needle disposed within the second operative portion. According to one feature of this embodiment of the suturing instrument, a first suture is attached to the first needle and a second suture is attached to the second needle. According to another feature of this embodiment, the suturing instrument includes a suture having a first end attached to the first needle and a second end attached to the second needle.

In a fifth embodiment according to the fifth aspect of the invention, the distal portion of the suturing instrument includes a first needle catch configured to receive a first needle; and a second needle catch configured to receive a second needle. Optionally, the first needle catch and the second needle catch form a unitary needle catch. At least one of the first needle catch and the second needle catch may define a retention slot including at least two flexible edges.

In a sixth embodiment according to the fifth aspect of the invention, the first operative portion of the distal portion defines a first needle port and the second operative portion of the distal portion defines a second needle port. In this embodiment, the distance between the first needle exit port and second needle exit port is laterally adjustable by deflecting at least one of the first operative portion and the second operative portion outwardly from the elongate body member. According to one feature of this embodiment, the suturing instrument includes a deflecting mechanism for adjusting the distance between the first needle exit port and the second needle exit port. A deflection actuator disposed opposite the distal portion of the elongate body member may be included for actuating the deflecting mechanism. The deflecting mechanism may include, for example, a wedge, a cam, an elbow linkage, a rotational separator, and a track-and-follower assembly.

Lastly, in general, in a sixth aspect, the invention features a suturing instrument that includes an elongate body member having a distal portion. The distal portion includes a needle catch. The suturing instrument also includes a cartridge that is disposed at least partially within the distal portion and houses a first needle and a second needle, as well as a needle deployment mechanism that is disposed at least partially within the elongate body member and is connectable sequentially to the first needle and the second needle for moving the first needle and then the second needle from the cartridge out of the distal portion to the needle catch. The cartridge may be removable from the distal portion of the elongate body member or integrally formed within the distal portion. Also, the distal portion of the elongate body member is optionally rotatable relative to a remainder of the elongate body member.

Further, in one embodiment of the sixth aspect of the invention, the needle deployment mechanism includes a needle carrier that is disposed at least partially within the distal portion of the elongate body member and is slidably movable out of the distal portion and an actuator coupled to the needle carrier and disposed opposite the distal portion of the elongate body member.

In another embodiment of the sixth aspect of the invention, the cartridge defines an exit aperture for receiving at least one of the first needle and the second needle. According to one feature of this embodiment, the cartridge further defines a loading slot connected to the exit aperture. At least one of the first needle and the second needle can be received in the loading slot. The second needle transitions from the needle loading slot to the exit aperture after the first needle is deployed from the cartridge. In one version of this feature, the suturing instrument includes a pusher for transitioning the second needle from the needle loading slot to the exit aperture after the first needle is deployed from the cartridge through the opening. Optionally, the pusher includes a push plate for contacting the second needle and a resilient member for biasing the push plate towards the exit aperture. In another version of this feature, the suturing instrument includes a suture having one end attached to the second needle, so that the second needle is transitioned from the loading slot to the exit aperture after the first needle is deployed from the cartridge by pulling on the free end of the suture. The suturing instrument may also include a means for pulling the free end of the suture optionally attached to the elongate body member and disposed opposite the distal portion thereof, such as, for example, a spool or a lever.

In yet another embodiment of the sixth aspect of the invention, the cartridge also contains a third needle. In this embodiment, the needle deployment mechanism is connectable sequentially to the first needle and the second needle and the third needle for moving the first needle and then the second needle and then the third needle from the cartridge out of the distal portion to the needle catch.

In still another embodiment of the sixth aspect of the invention, the suturing instrument includes a handle that is disposed opposite the distal portion of the elongate body member and at least partially houses the needle deployment mechanism.

The invention also features a method for placing sutures in multiple tissue sites. The method includes the step of providing a suturing instrument having an elongate body member with a distal portion. The distal portion of the suturing instrument includes a needle catch. The suturing instrument also has a cartridge disposed at least partially within the distal portion. The cartridge includes a first needle disposed within the cartridge and a second needle disposed within the cartridge. Also, the suturing instrument includes a needle deployment mechanism disposed at least partially within the elongate body member and connectable sequentially to the first needle and the second needle. The method of the invention further contemplates the steps of disposing the suturing instrument in a body, positioning the distal portion proximal to a first tissue site in the body, actuating the needle deployment mechanism thereby moving the first needle out of the cartridge to the needle catch, positioning the distal portion proximal to a second tissue site in the body without withdrawing the suturing instrument from the body, moving the second needle in the cartridge, and actuating the needle deployment mechanism thereby moving the second needle out of the cartridge to the needle catch.

In various embodiments according to the foregoing aspects of the invention, the elongate body member is adapted to access remote organs or tissue within a body. Also, the suturing instrument disclosed above may include one, two, or more bends.

Advantages and features of the present invention herein disclosed will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic plan view of one embodiment of a suturing instrument in accordance with the invention;

FIG. 6C is a schematic perspective view of the proximal portion of the suturing instrument of FIG. 6A;

FIG. 6D is a schematic perspective view of the deflection and rotation mechanisms of the suturing instrument of FIG. 6A;

FIG. 6I is a schematic cross-sectional view of the suturing instrument of FIG. 6E;

FIG. 6J is a schematic cross-sectional view of one embodiment of a locking mechanism for use with a suturing instrument in accordance with the invention;

FIG. 6K is a schematic cross-sectional view of an alternative embodiment of the locking mechanism of FIG. 6J;

FIG. 12A is a schematic perspective view of a suturing instrument configured for use with an endoscope in accordance with the invention;

FIG. 12B is a schematic perspective view of a distal portion of the suturing instrument of FIG. 12A attached to a sheath having a carrier drive wire disposed therein; and FIG. 12C is a schematic perspective view of a pivotable distal portion of the suturing instrument of FIG. 12A.

DESCRIPTION

Figure 1B:
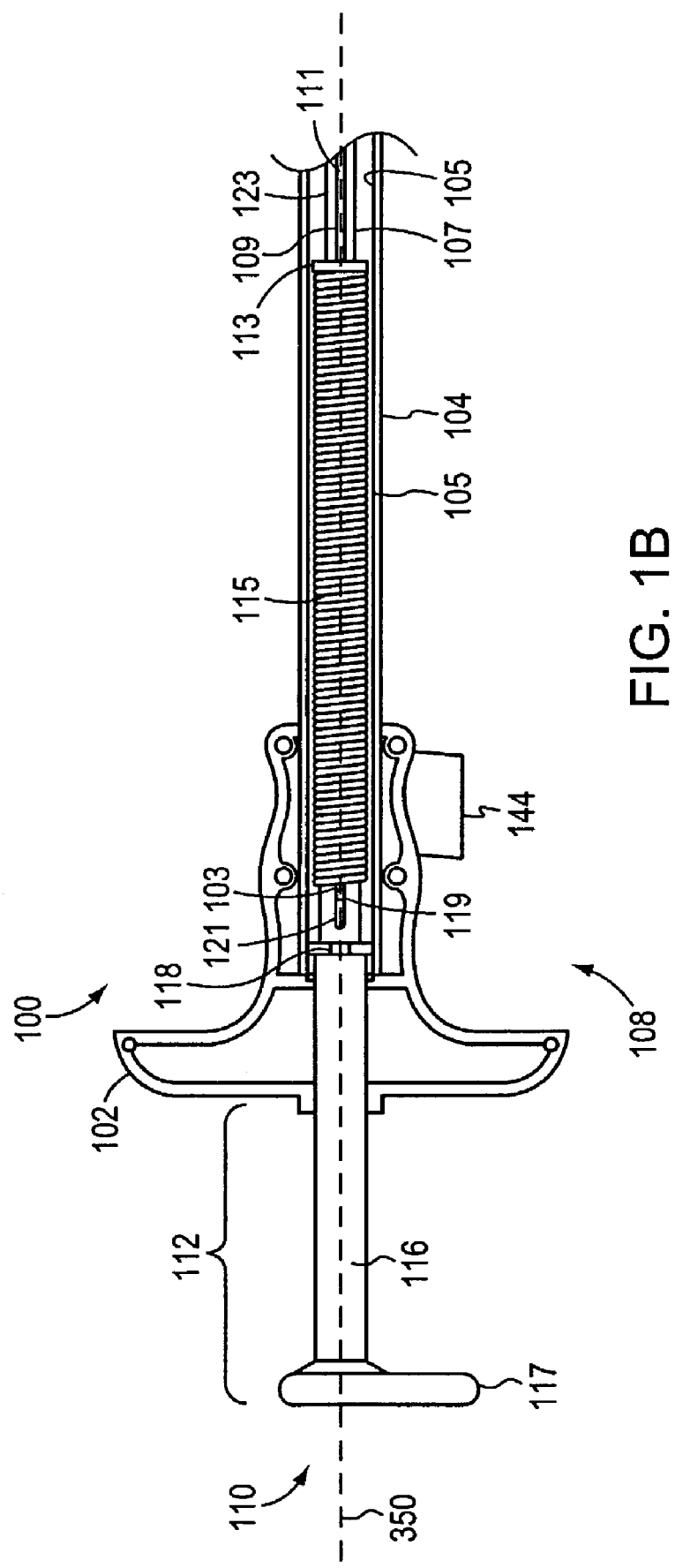
FIG. 1B is a schematic cross-sectional view of a proximal portion of the suturing instrument of FIG. 1A.

Referring to FIG. 1A, in one embodiment, a suturing instrument 100 includes a handle 102, an elongate body member 104, and a needle deployment mechanism 110 disposed within the elongate body member 104 and the handle 102. The suturing instrument 100 also includes a distal portion 106 and a proximal portion 108. The elongate body member 104 is mechanically coupled to the handle 102 at the proximal portion 108 and the suturing components are at least partially disposed within the distal portion 106 of the suturing instrument 100.

The handle 102 can take a variety of forms, for example, the handle 102 could be one of the types compatible with suturing systems available from Boston Scientific Corporation of Natick, Mass., in particular with the Capio® Push & Catch suturing system. A suture clip 144 may be coupled to the handle 102 or the elongate body member 104 and used to hold an end of one or more sutures 136 prior to placement in a patient. Generally, the needle deployment mechanism 110 extends longitudinally through the elongate body member 104 to the distal portion 106 of the suturing instrument 100, where the needle deployment mechanism 110 is coupled to a needle 128 (shown in FIG. 2A). The needle deployment mechanism 110 moves the needle 128 between a retracted position and a deployed position. One possible needle deployment mechanism 110 is shown in greater detail in FIGS. 1B and 1C.

Referring to FIG. 1B, in one embodiment, the proximal portion 108 of the suturing instrument 100 includes the handle 102, the elongate body member 104, the suture clip 144, and the needle deployment mechanism 110. The needle deployment mechanism 110 includes an actuator button 117 and a shaft 116 that together form an actuator 112. The needle deployment mechanism 110 also includes a bearing 118 and a button end 119 that defines a hole 121 formed therein. The hole 121 is preferably formed along the central longitudinal axis of the button end 119. The bearing 118 rides along the surface of a lumen 105 that is defined by the inside diameter of the elongate body member 104. A wireform 103 is inserted into the hole 121 of the button end 119, so that the wireform 103 is coupled to the actuator button 117. A spring 115 encircles the wireform 103, abuts the button end 119, and is compressed between the button end 119 and a spring washer 113. The spring washer 113 is seated upon a center tube 107. The center tube 107 is housed by the lumen 105 and is constrained in the distal portion 106. A pusher wire 111 is attached to the wireform 103 by means of a weld, a coupling, adhesive, or other means, and is slidably disposed within a guidance sleeve 109, the sleeve 109 being disposed within the surface of a lumen 123 defined by the inside diameter of the center tube 107.

In one embodiment, the pusher wire 111 is constructed of an elastic material having "superelastic" properties. Such a material may include alloys of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn. In the illustrative embodiment, the superelastic material is a nickel and titanium alloy, commonly known as Nitinol® available from Memry Corp of Brookfield, Conn. or SMA Inc. of San Jose, Calif., so chosen for its combination of properties that allow for bendability and high column strength when constrained. The ratio of nickel and titanium in Nitinol® may vary. One preferred example includes a ratio of about 50% to about 56% nickel by weight. Nitinol® also possesses shape retention properties.

Figure 1C:
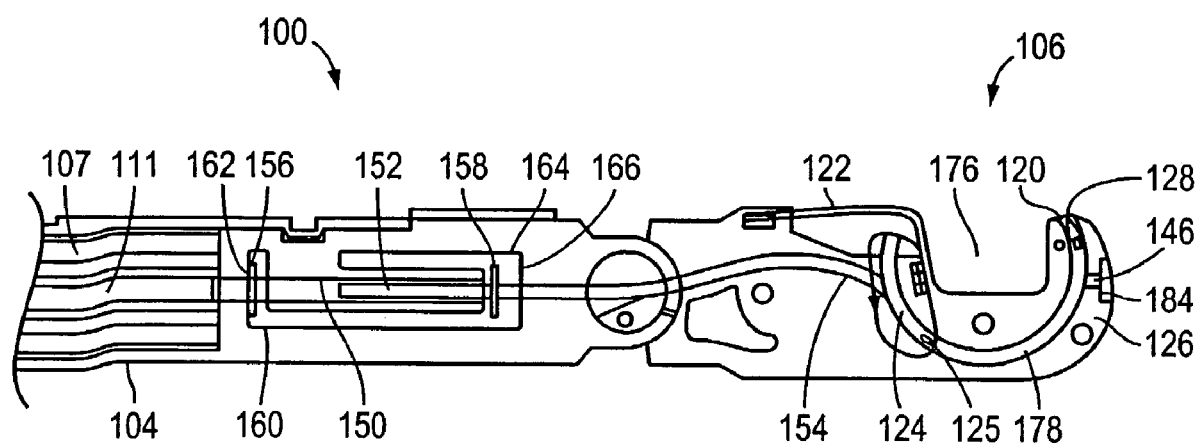
FIG. 1C is a schematic cross-sectional view of a distal portion of the suturing instrument of FIG. 1A.

Referring to FIG. 1C, the distal portion 106 of the elongate body member 104 includes the distal components of the needle deployment mechanism 110 (described in detail below), an operative portion 126, and a needle catch 122. In one embodiment, the operative portion 126 has an arcuate shape and partially encircles a suturing field 176. The operative portion 126 also defines a lumen 178 therein having a needle exit port 120 at an opening into the suturing field 176. A needle 128 is disposed in the needle exit port 120 and is held in place by a slight friction fit. In one embodiment, the suture 136 is attached to the needle 128. The free end of the suture 136 extends out of a suture slot 146.

Referring again to the needle deployment mechanism 110, the pusher wire 111 is attached by welding or other means to a coupling 150, which is slidably disposed within a track 152. The coupling 150 is attached to a carrier wire 154, which, by virtue of its attachment to the coupling 150, is also slidably disposed within the track 152. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

The carrier wire 154 is mechanically coupled to an extendable needle carrier 124 by welding, coupling, use of adhesives, or by other means. The needle carrier 124 is slidably disposed in the lumen 178 of the operative portion 126 and has a lumen 125 formed at a distal end of the needle carrier 124. The lumen 125 is dimensioned to releasably receive the non-penetrating end of the needle 128. The needle carrier 124 is configured to push the needle 128 out of the needle exit port 120 through tissue proximate the suturing field 176, and into the needle catch 122, as will be described in further detail below. In one embodiment, the needle 128 is held within the lumen 125 by a slight friction fit.

Figure 2A:
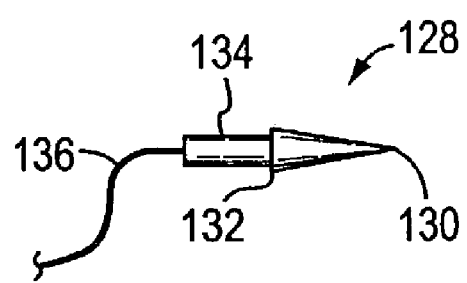
FIG. 2A is a schematic plan view of a needle coupled to a suture for use in a suturing instrument in accordance with the invention.

FIG. 2A depicts one embodiment of the needle 128 for use in a suturing instrument in accordance with the invention. In this embodiment, the needle 128 includes a penetrating tip 130 and a shaft 134 coupled to the tip 130, thereby forming a shoulder 132. The shaft 134 is coupled to the suture 136. Other configurations of the needle 128 can also be used without deviating from the scope of the invention. As shown in FIG. 1C, in one embodiment, when the needle 128 is disposed in the needle exit port 120, the free end of the suture 136 extends out of a needle carrier suture slot 148 and the suture slot 146.

Figure 2B:
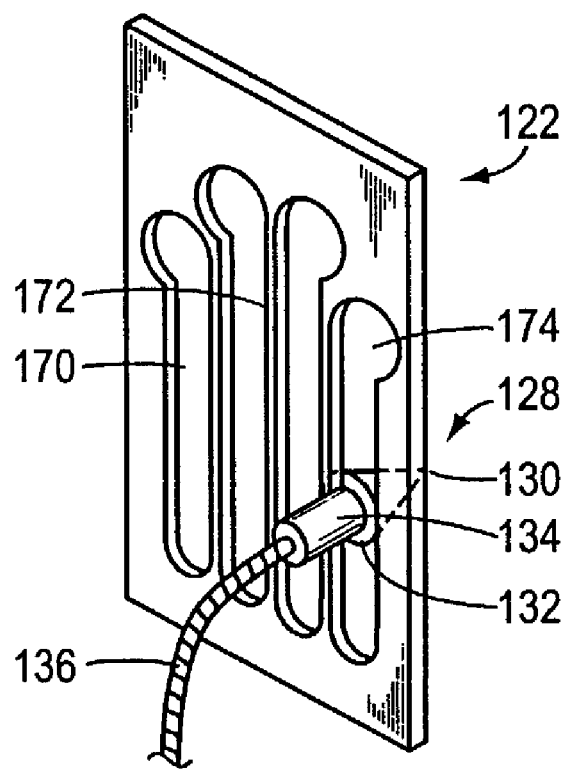
FIG. 2B is a schematic perspective view of a needle catch for use with the suturing instrument of FIG. 1A.

Referring to FIG. 2B, the needle catch 122 includes openings 170 defined by successive ribs 172. When the needle catch 122 receives the needle 128 coupled to the suture 136 through opening 170, the ribs 172 deflect slightly to allow the needle 128 to pass through. After the shoulder 132 has passed the ribs 172, the ribs 172 spring back to their original position defining the openings 170, and the needle 128 remains captured in the needle catch 122. The openings 170 are chosen to be smaller in dimension than the shoulder 132. This causes the needle catch 122 to retain the needle 128, because the flat rear surface of the shoulder 132 prevents the needle 128 from passing back through the opening 170. When it is necessary to remove the needle 128 from the needle catch 122, the needle 128 may be moved toward an enlarged portion 174 of the opening 170. The enlarged portion 174 is sized to allow the shoulder 132 to pass through without resistance. The needle catch 122 may be constructed of thin stainless steel of high temper, such as ANSI 301 full hard. The needle catch 122 may be fabricated by means of stamping, laser machining, or chemical etching.

Referring again to FIGS. 1A–1C and 2A–2B, in operation, a user (such as a physician or other medical personnel) actuates the needle deployment mechanism 110 by pushing on the button 117, which, via the attachment to the wireform 103, is attached to the pusher wire 111, moves the coupling 150 along the track 152 concomitantly moving the carrier wire 154, which in turn slidably moves the needle carrier 124 through the lumen 178 towards the needle exit port 120. The user continues to push the button 117 until the needle carrier 124 receives the needle 128 in the lumen 125, and further until the needle 128 penetrates tissue proximate the suturing area 176 and then enters and is retained in the needle catch 122. Then, the user releases the button 117 and the spring 115 urges the button 117 proximally, thereby moving the pusher wire 111, the coupling 150, the carrier wire 154, and the needle carrier 124 proximally along with the button 117 to the retracted position. As the needle carrier 124 moves back to the retracted position, the needle 128 slides out of the lumen 125 and the needle is released from the needle carrier 124.

In one embodiment, after one or more sutures 136 have been placed, the user withdraws the suturing instrument 100 from the patient. The user then detaches one or more sutures 136 from one or more needles 128 and ties a knot or knots in the sutures 136. The user can then use a knot pusher 184 to push one or more knots into the patient as the knots are tightened.

The suturing instrument's component materials should be biocompatible. For example, the handle 102, the elongate body member 104, and portions of the needle deployment mechanism 110 may be fabricated from extruded, molded, or machined plastic material(s), such as polypropylene, polyethylene, polycarbonate, or glass-filled polycarbonate. Other components, for example the needle 128, may be made of stainless steel. Other suitable materials will be apparent to those skilled in the art. The material(s) used to form the suture should be biocompatible. The surgeon will select the length, diameter, and characteristics of the suture to suit a particular application. Additionally, the mechanical components and operation are similar in nature to those disclosed in U.S. Pat. Nos. 5,364,408 and 6,048,351, and commonly owned U.S. patent application Ser. No. 10/210,984, each of which is incorporated by reference herein in its entirety.

Figure 3A:
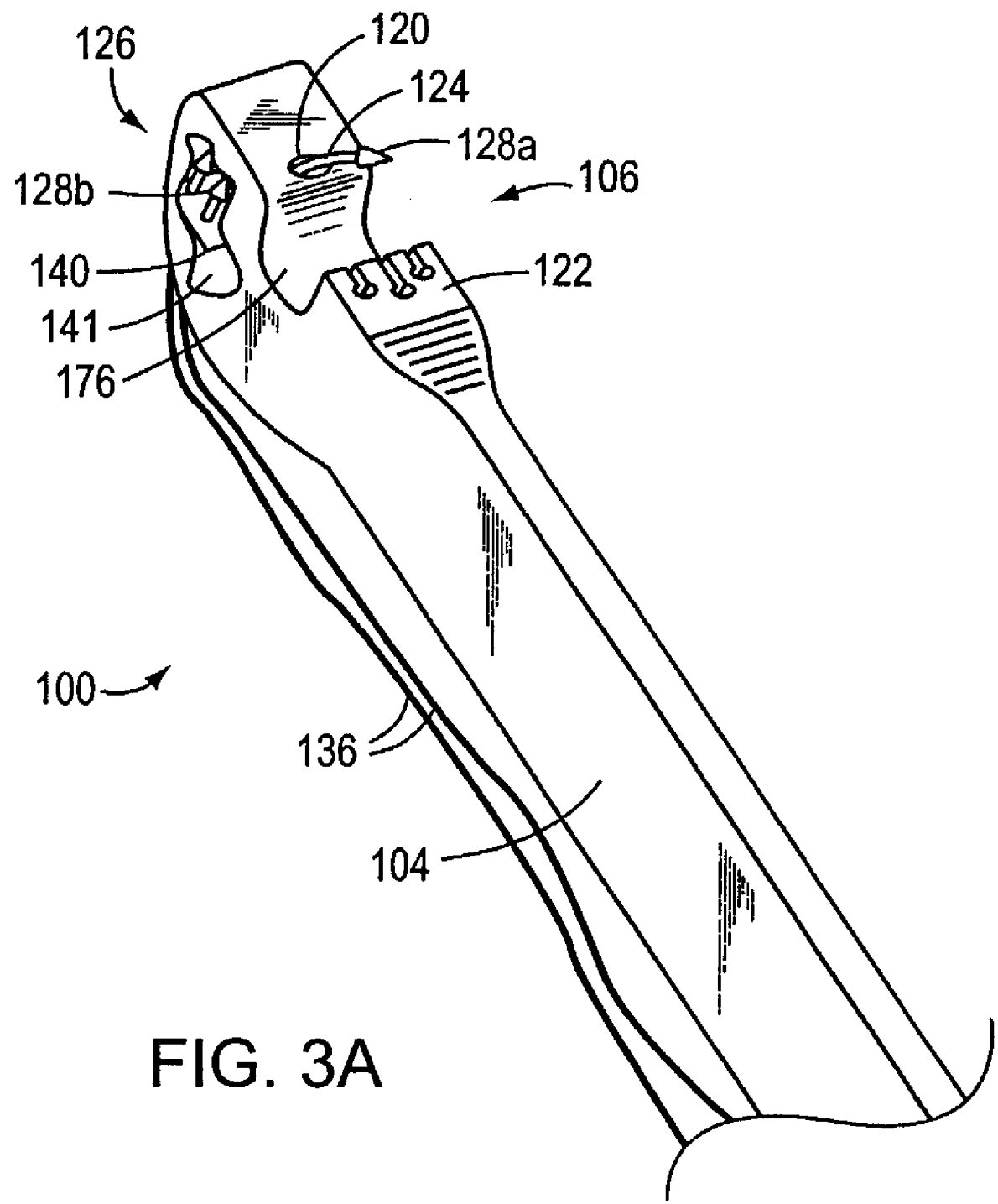
FIG. 3A is a schematic perspective view of a distal portion of a suturing instrument including a multi-load needle cartridge in accordance with the invention.
Figure 3B:
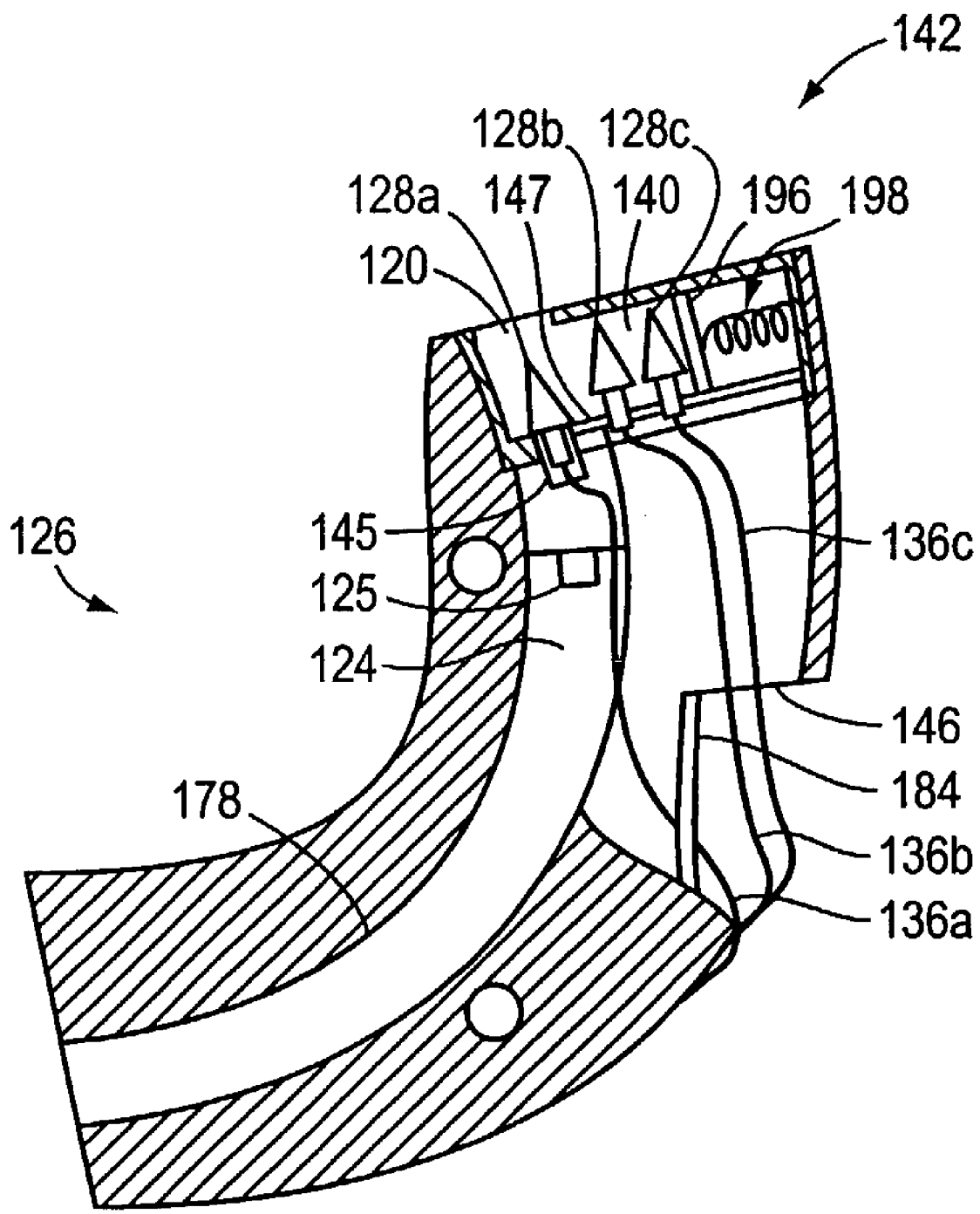
FIG. 3B is an enlarged cross-sectional view of the suturing instrument of FIG. 3A.

FIGS. 3A and 3B depict two embodiments of a suturing instrument having a multi-load cartridge 140 in accordance with the invention. Such a suturing instrument advantageously allows the user to place multiple sutures without removing the suturing instrument from the surgical site. According to both embodiments, the suturing instrument 100 includes the cartridge 140 that houses two or more needles 128 disposed therein. Referring to FIG. 3A, the cartridge 140 is integrally formed within the distal portion 106. In this embodiment, the distal portion 106 defines a sidewall access opening 141 to allow the user to load one or more needles 128 into the cartridge 140. Referring to FIG. 3B, the cartridge 140 is either integrally formed or removably disposed at a distal end 142 of the operative portion 126. Having a removable cartridge allows the user to choose a cartridge having a specific number of needles for a specific application. Also, the suturing instrument 100 may be reusable with different needle cartridges.

Referring still to FIG. 3B, the multi-load needle cartridge 140 defines an exit aperture 145 and a needle loading slot 147. The multi-load needle cartridge 140 is designed to hold essentially any number of needles, for example, 2–20 needles. The multi-load needle cartridge 140 is preloaded and capable of feeding the needle and suture assembly into the needle carrier 124. In one embodiment, the cartridge 140 can be reloaded by the user in situ by adding needles 128 using, for example, the sidewall access opening 141 (FIG. 3A) or the exit port 120 (FIG. 3B). The multi-load needle cartridge 140 may include a push plate 196 and a spring 198 that biases the push plate 196 towards the exit aperture 145.

Both embodiments operate in essentially the same manner, enabling a user to place multiple sutures 136 in a patient without removing the suturing instrument 100 from the surgical site. As described above, the preloaded multi-load needle cartridge 140 can include one or more needles 128 each with the suture 136 coupled thereto. Referring to FIG. 3B, in one embodiment, the needle cartridge 140 includes three needles 128a, 128b, 128c. Sutures 136a, 136b, 136c extend out of the suture slot 146. Alternatively, the sutures 136 may run through the elongate body member 104. The first needle 128a is disposed in the exit aperture 145, and the remaining needles 128b, 128c are disposed in the loading slot 147.

The needle carrier 124, which is part of the needle deployment mechanism 110, is sequentially connectable to the needles 128 stored in the cartridge 140. This means that each needle 128 stored in the needle cartridge 140 is connected to, and then deployed by, the needle carrier 124 one at a time in the order the needles 128 are dispensed from the needle cartridge 140.

In operation, the user inserts the elongate body member 104 into a patient and orients the elongate body member 104 so that the tissue to be sutured is disposed proximate the suturing field 176 and the needle exit port 120 is proximate to or in contact with the tissue. The user then pushes the button 117 (FIG. 1B), as described above. Pushing the button 117 causes the needle carrier 124 to receive the needle 128a in the lumen 125 and then to extend out of the needle exit port 120 and push the needle 128a through the tissue. As the first needle 128a is pushed through the tissue, the first needle 128a pulls the first suture 136a through the tissue. As the user continues to push the button 117, the needle carrier 124 continues to advance out of the needle exit port 120 and directs the first needle 128a and the first suture 136a toward the needle catch 122. The user continues to push the button 117 until the first needle 128a contacts and becomes captured by the needle catch 122. The user then retracts the needle carrier 124 by releasing the button 117, as previously described.

After the user retracts the needle carrier 124, the first needle 128a and the first suture 136a are left captured within the needle catch 122, with the first suture 136a extending through the tissue. When the needle carrier 124 returns to a fully retracted position, the spring 198 causes the needle push plate 196 to push the second needle 128b into the exit aperture 145. The needle 128b is thereby forced through the loading slot 147 and either into the lumen 125 of the needle carrier 124 or in position to be captured by the needle carrier 124. The second suture 136b extends out of the suture slot 146. The user then advances the needle carrier 124 as described above until the second needle 128b is captured by the needle catch 122. The user then retracts the needle carrier 124 as described above leaving the second needle 128b and the second suture 136b captured by the needle catch 122. This procedure can be repeated for the third needle 128c, or for as many needles as may be stored in the needle cartridge 140. After one or more sutures 136 have been placed, the user withdraws the suturing instrument 100 from the patient. The user detaches the suture(s) 136 from the needle(s) 128 and ties a knot or knots in the suture(s) 136. The user can then use the knot pusher 184 to push the knot(s) in the patient as the knot(s) is tightened.

Alternatively, other mechanisms could be used to advance the needle 128 from the needle cartridge 140 to the carrier 124. In one embodiment, the needles 128 in the needle cartridge 140 are held in the loading slot 147 by a friction fit and are pushed into the exit aperture 145 when the needle push plate 196 is activated by the user. For example, instead of the spring 198, a dispensing control rod coupled to a button on the handle 102 and the push plate 196 may be provided. Alternatively, a spring release mechanism coupled to the spring 198 and a button on the handle 102 may be provided to enable the user to release the spring 198 so that the push plate loads the needle 128 into the exit aperture 145 to be received in the lumen 125 of the needle carrier 124. In another embodiment, the user may load the needle 128 into the exit aperture 145 by pulling the free end of the suture 136. In yet another embodiment, the suturing instrument 100 may include a means for pulling the free end of the suture 136 such as, for example, a spool or a lever attached to the elongate body member and disposed, for example, on or within the handle 102.

Figure 4A:
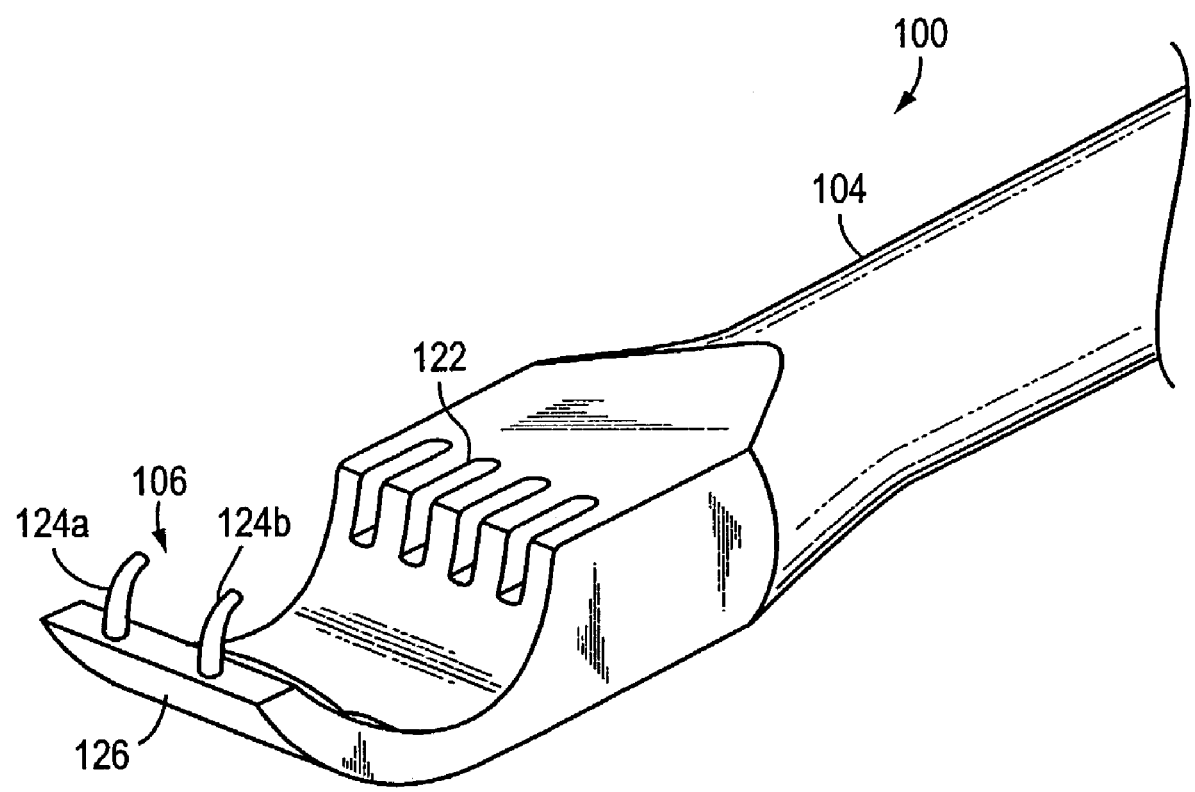
FIG. 4A is a schematic perspective view of a distal portion of a multi-needle suturing instrument in accordance with the invention.

Referring to FIG. 4A, in another embodiment, the operative portion 126 of the distal portion 106 of the suturing instrument 100 includes a mechanism for deploying two or more needles 128. The needles 128 can be deployed sequentially or simultaneously. The deployment mechanism includes a separate needle carrier 124a, 124b for each needle 128. The handle 102 can include one button 117 to advance both needles 128 or the handle 102 can include two buttons 117a, 117b to advance the needles 128 sequentially or simultaneously (if pressed at the same time). Passing two single armed needles into an incision site enables a user to place, for example, two ligating sutures simultaneously, withdrawing the device, and tying two knots. Ligating between the sutures is possible in a shorter time-frame.

In operation, this embodiment functions largely the same way as the embodiments previously described. For simultaneous advancement, the user advances the needle carriers 124 by pressing the button(s) 117 (FIG. 1A) until the needles 128 are driven through the tissue and captured by the needle catch 122. After the needles 128 are captured in the needle catch 122, the needle carriers 124 are retracted. For sequential advancement, the user advances one needle carrier 124a by pressing one button 117a until the first needle 128a is driven through the tissue and captured by the needle catch 122. The user then retracts the first needle carrier 124a. The user then advances the second needle carrier 124b by pressing the second button 117b until the second needle 128b is driven through the tissue and captured by the needle catch 122. The user then retracts the second needle carrier 124b.

Figure 4C:
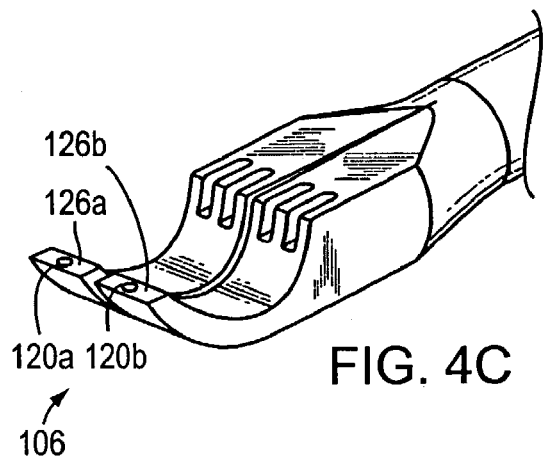
FIG. 4C is an enlarged schematic perspective view of the operative portions of the suturing instrument of FIG. 4B in an aligned position.
Figure 4B:
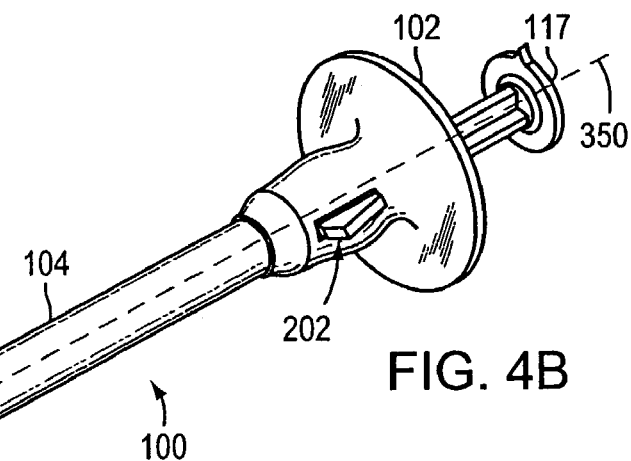
FIG. 4B is a schematic perspective view of an alternative multi-needle suturing instrument having two operative portions in accordance with the invention.
Figure 4D:
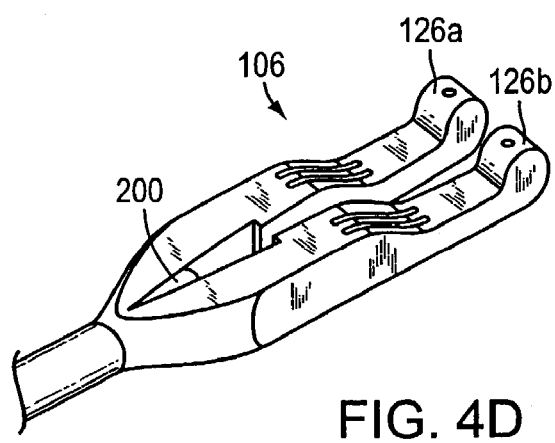
FIG. 4D is an enlarged schematic perspective view of the operative portions of the suturing instrument of FIG. 4B in a spread position.

Referring to FIGS. 4B–4D, in another embodiment, the distal portion 106 includes two separate operative portions 126a, 126b separated a wedge 200. The operative portions 126a, 126b include the needle exit ports 120a, 120b that are deflectable or spreadable outward relative to the elongate member 104 to adjust the distance between the exit ports 120a, 120b. The user may control the amount of separation between the operative portions 126a, 126b and, therefore, the distance between the exit ports 120a, 120b with a control lever 202 in the handle 102. Other mechanisms that can be used to deflect the operative portions 126a, 126b include, but are not limited to, a cam or link, an elbow linkage, a rotational separation along a longitudinal axis 350 of the device, a pre-made track and follower assembly, or a manual separator. In a particular embodiment, the user actuates the control lever 202, thereby advancing the wedge 200 and widening the space between the two operative portions 126a, 126b.

Figure 4E:
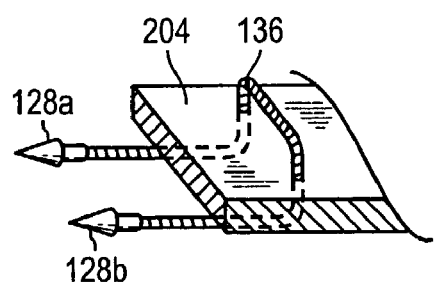
FIG. 4E is a schematic perspective view of a single suture placement in tissue.
Figure 4F:
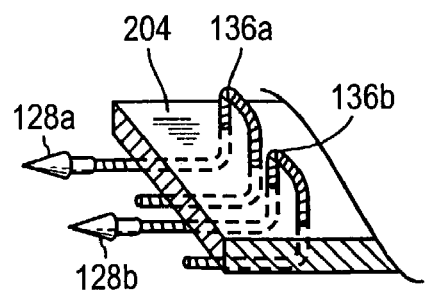
FIG. 4F is a schematic perspective view of a double suture placement in tissue.

One benefit of the embodiments depicted in FIGS. 4A–4D and described above is that spreading the operative portions 126a, 126b allows a user to create a controlled or predetermined distance between the needle carriers' tissue entrance points. This feature enables the placing of sutures 136 at different spacing sequences. In addition, these embodiments also provide a means to place a double-armed suture (a suture with a needle at each end) in a patient. Referring to FIGS. 4E and 4F, the needle deployment mechanism 110 generally functions the same way as previously described and can be used to place a single suture 136 coupled to two needles 128a, 128b through tissue 204 (FIG. 4E) or to place two sutures 136a, 136b coupled to two needles 128a, 128b, respectively (FIG. 4F) through tissue 204. Referring to FIG. 4E, where a single suture 136 is attached to the two needles 128a, 128b, the suture 136 is placed perpendicularly to the longitudinal axis 350 of the suturing instrument. Referring to FIG. 4F, where separate sutures 136a, 136b are attached to each of the two needles 128a, 128b, the sutures 136a, 136b can be placed in essentially any orientation relative to the longitudinal axis 350 of the suturing instrument.

Referring to FIGS. 5A–5H, in yet another embodiment, the suturing instrument 100 is modified to allow the user to place a so-called "whip stitch," i.e., a continuous running suture. Typically, the suturing instrument must be removed from the surgical site so the user may disengage the needle from the needle catch and either reload the existing needle into the needle carrier or load a new needle and suture into the instrument. In this embodiment, the user can remove the needle from the catch and reload the needle into the needle carrier without removing the suturing instrument 100. This allows the user to place a running stitch. This embodiment may be combined with any number of the other embodiments described herein.

Generally, the instrument is used to secure tissue with a continuous running suture by passing the suture through tissue, catching the suture needle, ejecting the needle from the catch in situ, and reloading the needle into the carrier. The suturing instrument 100 essentially operates in the same manner as the other instruments described herein. The instrument is modified, however, to add a needle reloading mechanism 205 described in detail below that, when advanced, pushes the needle 128 along the needle catch 122 to an opening that permits the needle to be discharged from the catch 122. The needle 128 can be discharged by, for example, pulling on the suture 136. Continued pulling on the suture 136 can reposition the needle 128 into the end of the needle carrier 124. The reloaded carrier 124 can then be advanced again, continuing suture placement through multiple tissue passes, resulting in a whip stitch.

Figure 5A:
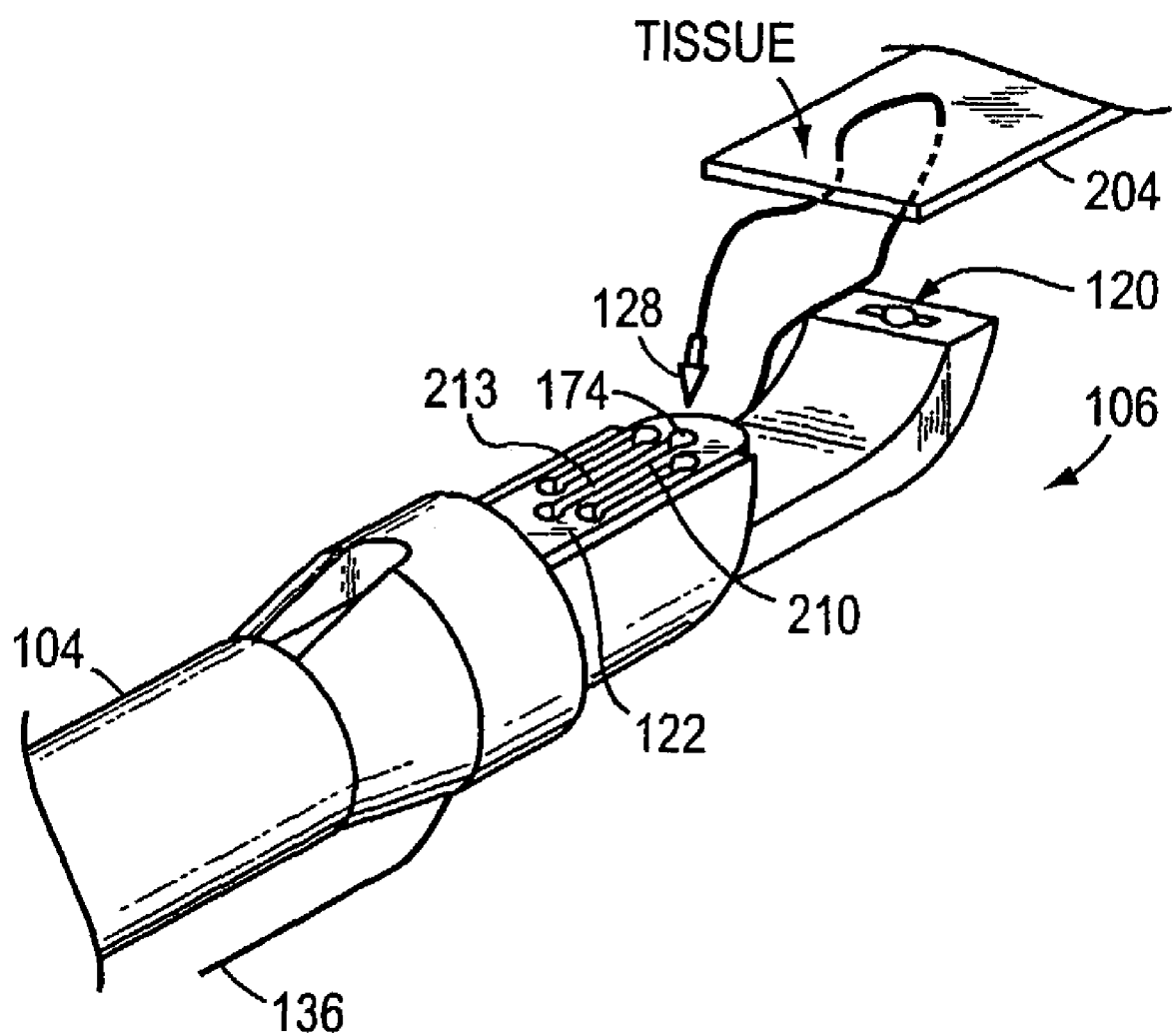
FIG. 5A is a schematic cross-sectional perspective view of a distal portion of a suturing instrument including a needle reloading mechanism in accordance with the invention.

FIG. 5A depicts the distal portion 106 of the suturing instrument 100. The needle carrier 124 and needle catch 122 are disposed in the distal portion 106. The needle catch 122 is similar to the catch described hereinabove with respect to FIG. 2B; however, the catch 122 is slightly modified to include two protrusions 210 disposed between the ribs of the center opening 213 to create a narrow portion in the opening 213. The protrusions 210 prevent the needle 128 from moving to the larger opening, i.e., the needle reloading aperture 174, in the catch 122 before the suturing instrument 100 is ready for reloading. In one embodiment, the needle catch 122 is slidably movable towards the needle exit port 120.

Figure 5B:
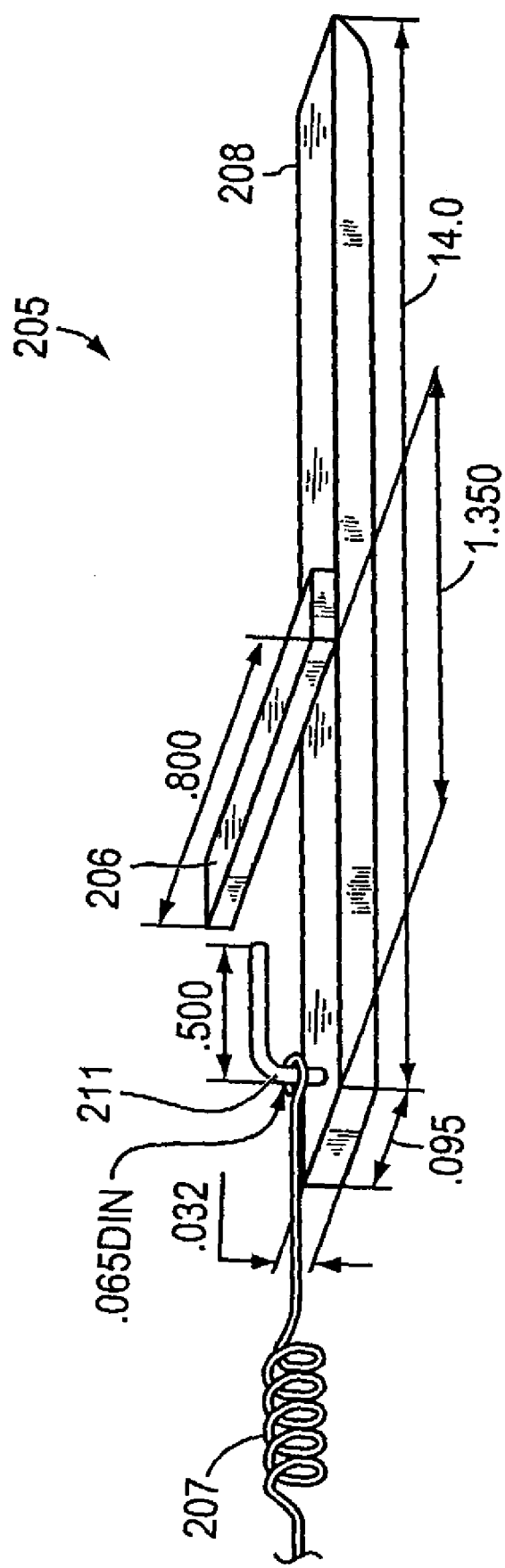
FIG. 5B is a schematic perspective view of a pusher rod for use with the suturing instrument of FIG. 5A.
Figure 5C:
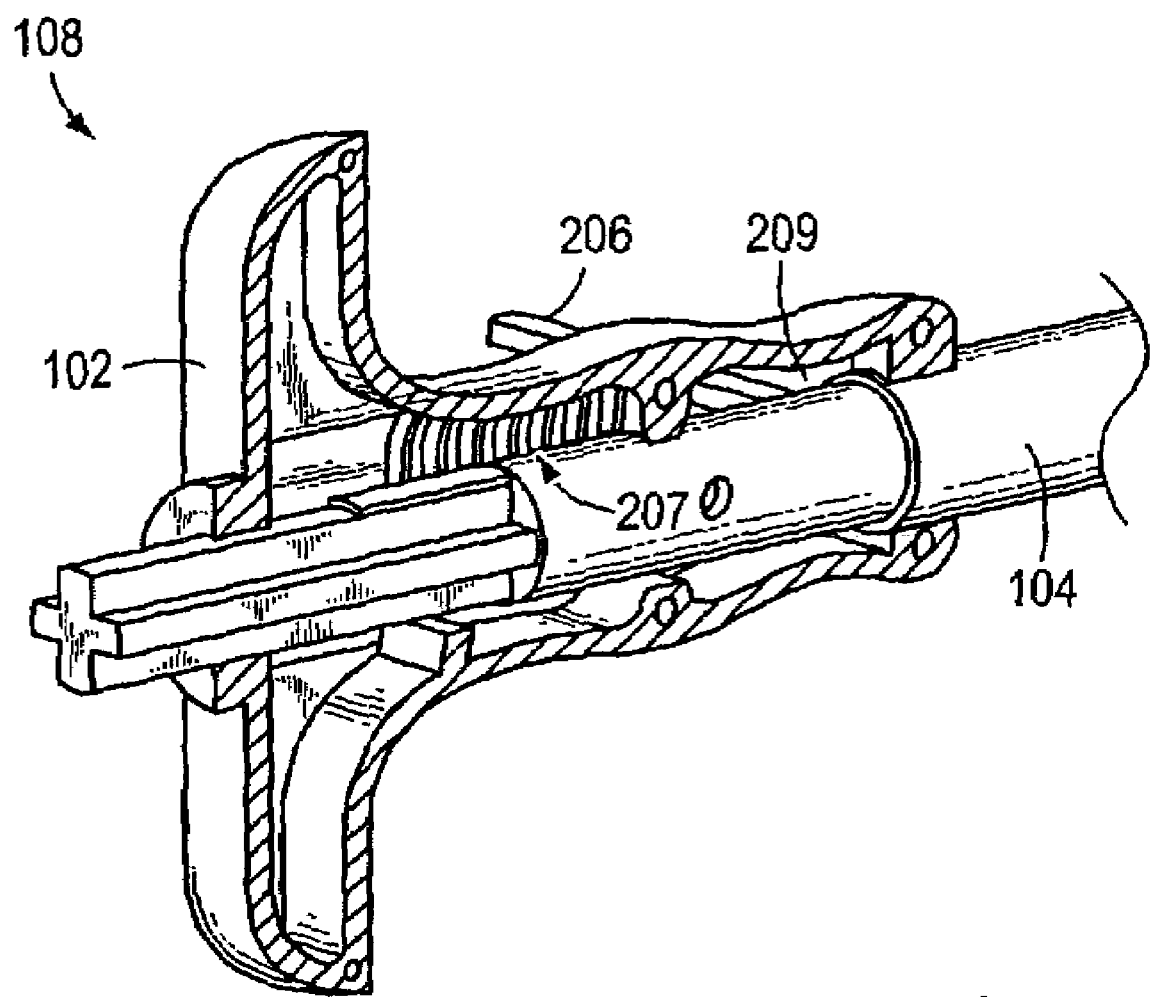
FIG. 5C is a schematic cross-sectional perspective view of a proximal portion of the suturing instrument of FIG. 5A.

FIG. 5B depicts a needle reloading mechanism 205. The mechanism 205 includes a pusher rod 208 and an actuator 206. The actuator 206 is generally perpendicularly disposed relative to the rod 208 and is attached to the rod 208 by, for example, welding or other attachment means. Additionally, the mechanism 205 includes a hook 211 that couples to a spring 207 located within the handle 102 (FIG. 5C). The spring 207 acts to return the mechanism 205 to its original position once the actuator 206 is released. In a particular embodiment, the mechanism 205 is slidably disposed within the suturing instrument 100.

Referring to FIG. 5C, the proximal portion 101 of the suturing instrument 100 is modified compared to the embodiment shown in FIG. 1A. Specifically, the handle 102 is modified to house at least a portion of the mechanism 205, as well as to include a slot 209 to house the actuator 206.

Figure 5D:
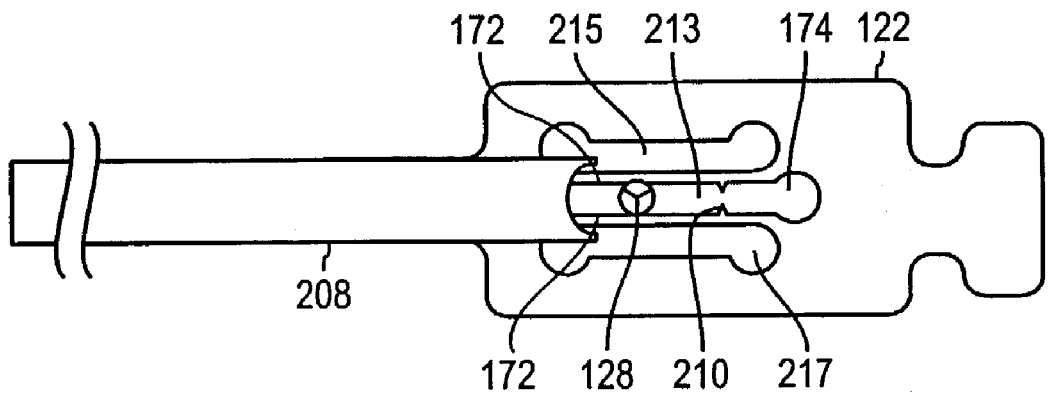
FIGS. 5D–5F are schematic plan views of the needle reloading mechanism of the suturing instrument of FIGS. 5A–5C in operation.
Figure 5E:
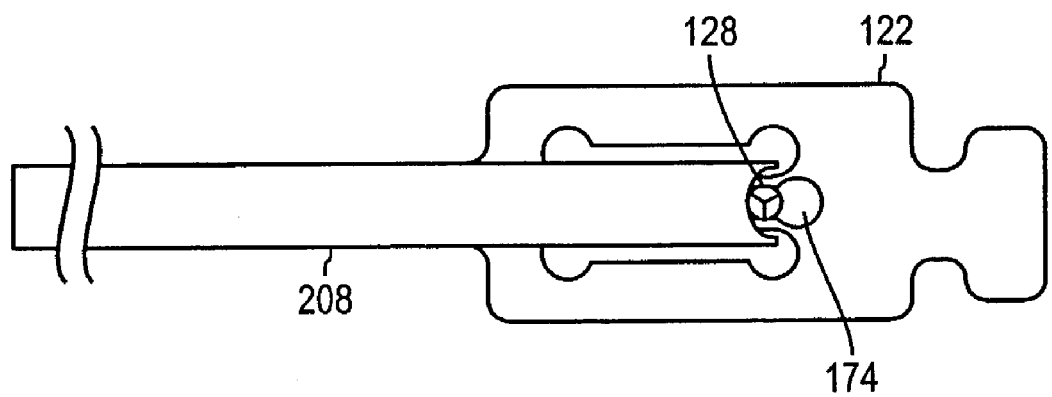
Figure 5F:
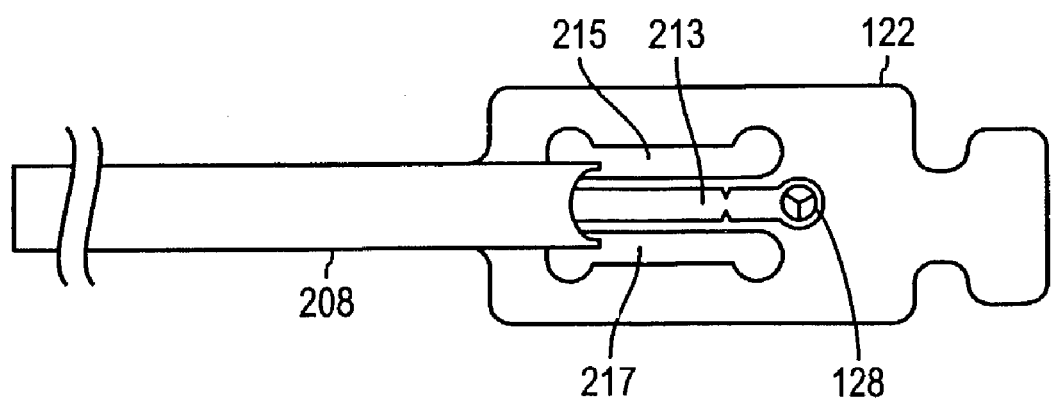

FIGS. 5D–5F are enlarged partial views of the needle catch 122 and pusher rod 208. As shown, the needle 128 is held within the center opening 213 of the catch 122 between two ribs or flexible edges 172. The pusher rod 208 includes a concave distal end that at least partially surrounds the needle 128 when the rod 208 is advanced into contact with the needle 128 (FIG. 5E). The pusher rod 208 pushes the needle 128 along the center opening 213 to the larger opening 174. The needle 128 is moved past the protrusions 210 by the force of the pusher rod 208. The force causes the ribs 172 to spread slightly to allow the needle 128 to pass. When the pusher rod 208 is fully advanced, the needle 128 will be positioned within the reloading aperture 174 (FIG. 5F). Alternatively, the needle 128 could be held within one of the lateral openings 215, 217 in a catch 122 further modified to include protrusions 210 in the lateral openings 215, 217. The pusher mechanism 205 can also be modified to push a needle 128 held in one or both of the lateral openings 215, 217.

Figure 5G:
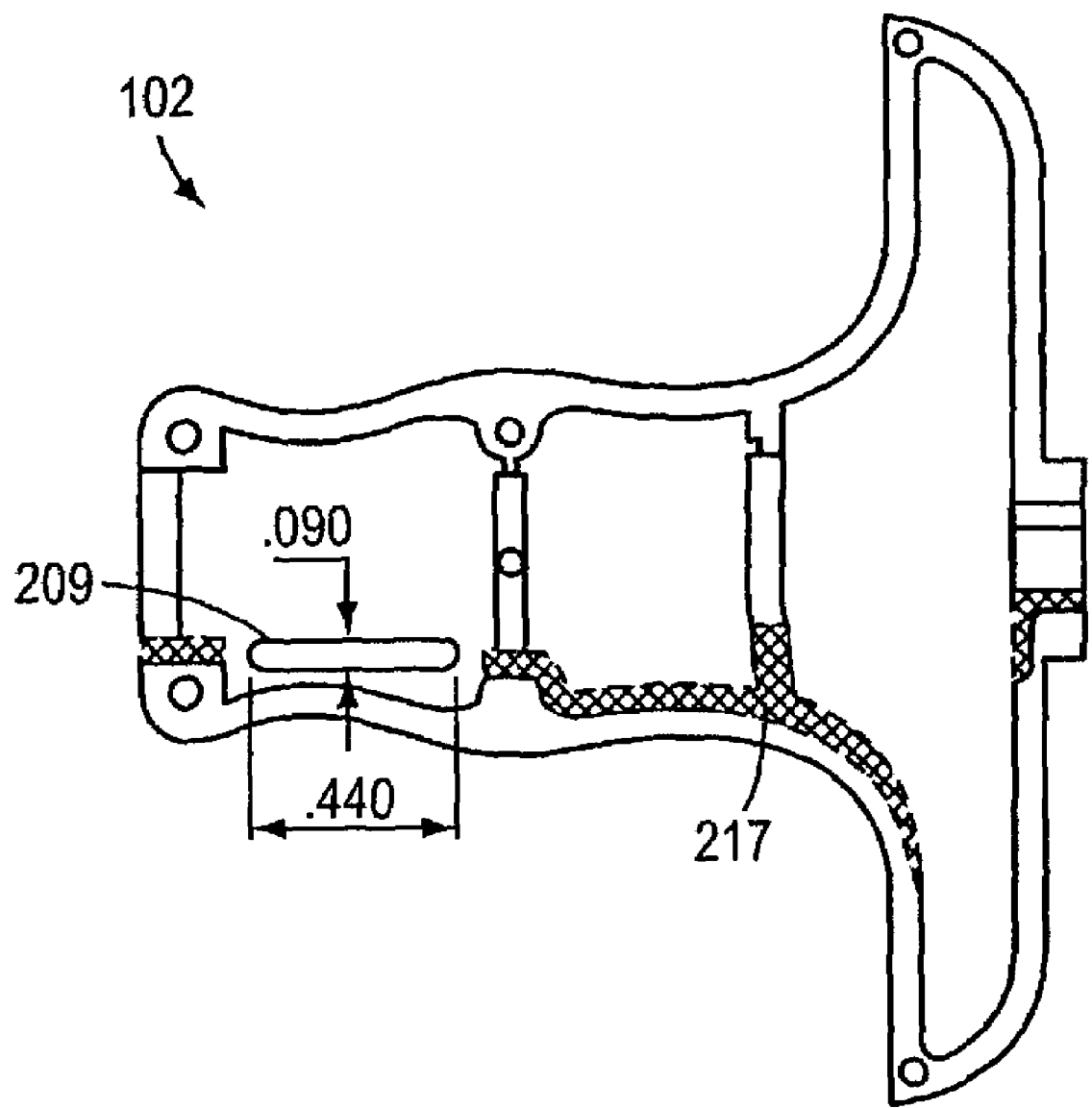
FIG. 5G is a schematic cross-sectional view of a modified handle for use with the suturing instrument of FIGS. 5A–5C.

FIG. 5G depicts the modified handle 102. As described hereinabove, the handle 102 includes the slot 209 for the actuator 206 and a void 217 for housing the proximal portion of the rod 208 and the spring 207 and hook 211. While the actuator 206 described herein is slidably disposed within the handle 102, other mechanical linkages are contemplated, for example, a push button and push wire assembly. The dimensions shown are for illustrative purposes only and are not meant to be limiting.

Figure 5H:
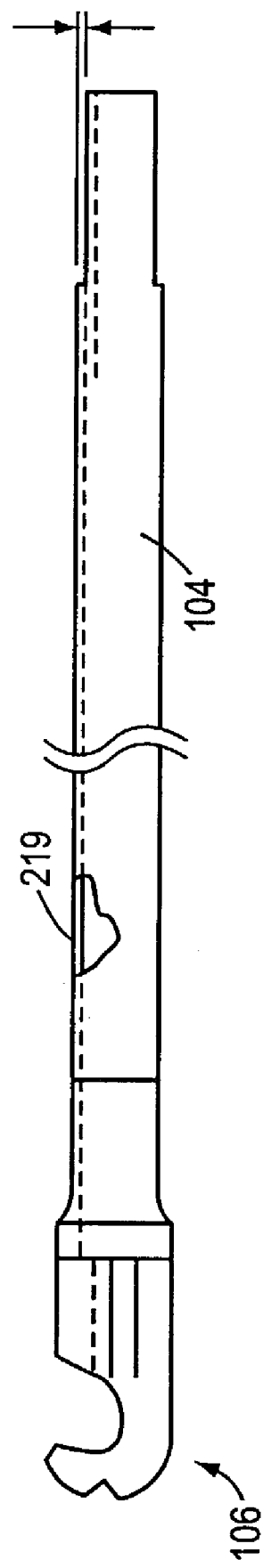
FIG. 5H is a schematic plan view of a modified elongate body member for use with the suturing instrument of FIGS. 5A–5C.

FIG. 5H depicts the modified elongate body member 104 compared to the embodiment depicted in FIG. 1A. The body member 104 is modified to house at least partially the pusher mechanism 205, specifically the pusher rod 208. The body member 104 includes a slot 219 that runs substantially the entire length of the body member 104. The pusher rod 208 is slidably disposed within the slot 219.

Operation of the instrument is described generally with reference to FIGS. 5A–5H. The basic operation is similar to that described hereinabove with reference to FIGS. 1A–1C, insofar as the user presses the button 117 thereby advancing the needle carrier 124 and pushing the needle 128 into the catch 122. After the user drives the needle through the tissue 204 and into the catch 122, the user positions the distal portion 106 of the suturing instrument 100 so that the tissue 204 is no longer in the surgical field 176. During operation, the suture 136 is preferably maintained in tension. A free end of the suture 136 remains outside of the surgical site and accessible to the user. Next, the user advances the needle reloading mechanism 205 into contact with the needle 128 by pushing the actuator 206 distally. Once the pusher mechanism 205 is fully advanced, the needle 128 is positioned within the needle reloading aperture 174. In this position, the free end of the suture 136 can be pulled to release the needle 128 from the catch 122 and, in turn, lead the needle 128 into the needle carrier. In addition, the needle carrier can be partially advanced to assist reloading of the needle 128 into the carrier. Also, the distal end of the needle carrier 124 can be modified to facilitate reloading. For example, the distal end of the carrier 124 and the lumen 125 could be enlarged to create a sufficient lead in for recapturing the needle 128. Further, as described above, the needle catch 122 may be slidable distally to position the needle 128 close to the carrier 124 before releasing the needle 128. After the needle 128 is recaptured in the lumen 125 of the needle carrier 124 and the needle carrier 124 is fully retracted into the operative portion 126, the user maneuvers the suturing instrument 100 and/or the tissue 204 so that the tissue 204 is disposed again proximate the suturing field 176 and the exit port 120 is proximate to the next stitching position in the tissue 204.

Figure 6A:
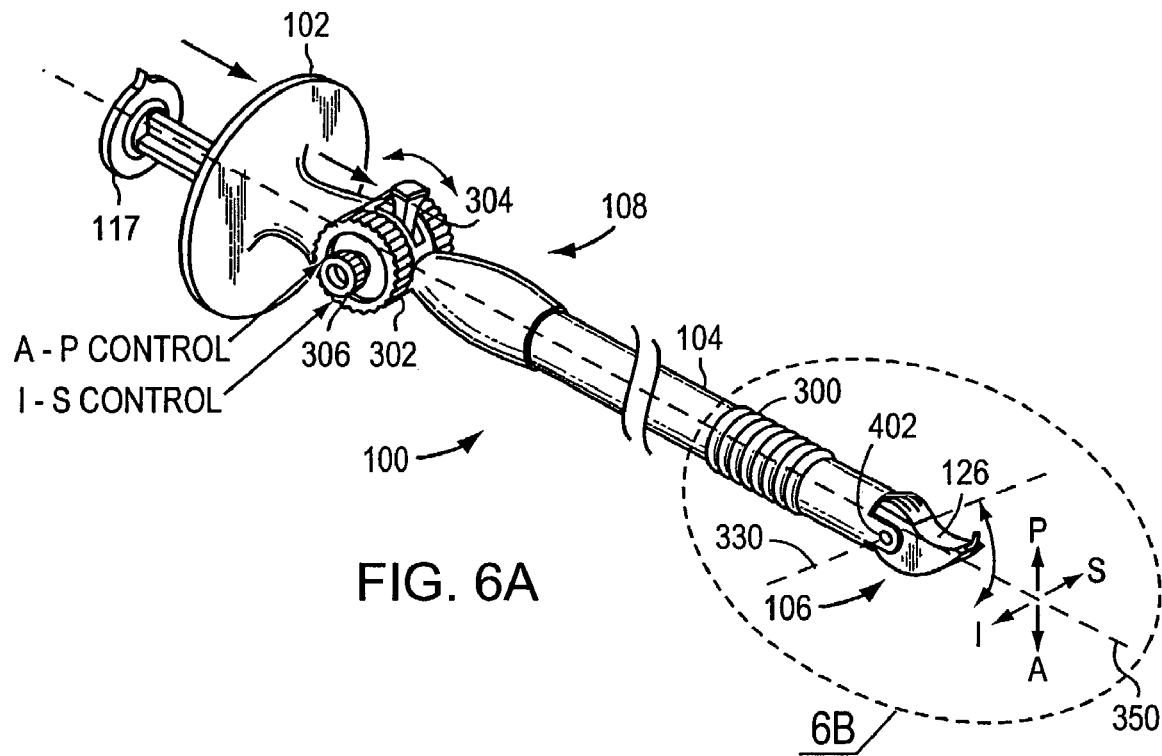
FIG. 6A is a schematic perspective view of one embodiment of a suturing instrument having a deflectable and pivotable distal portion in accordance with the invention.
Figure 6B:
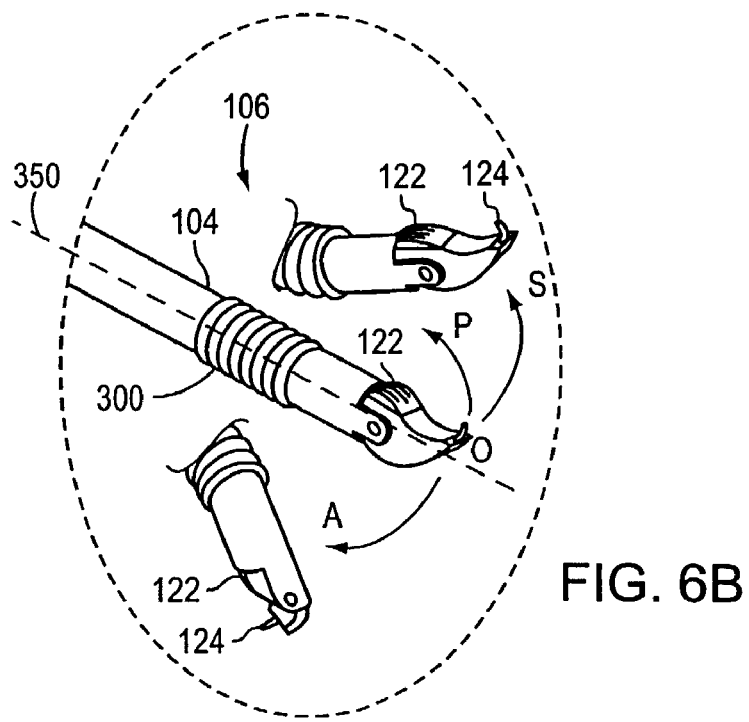
FIG. 6B is an enlarged schematic perspective view of the deflectable distal portion of the suturing instrument of FIG. 6A.
Figure 6E:
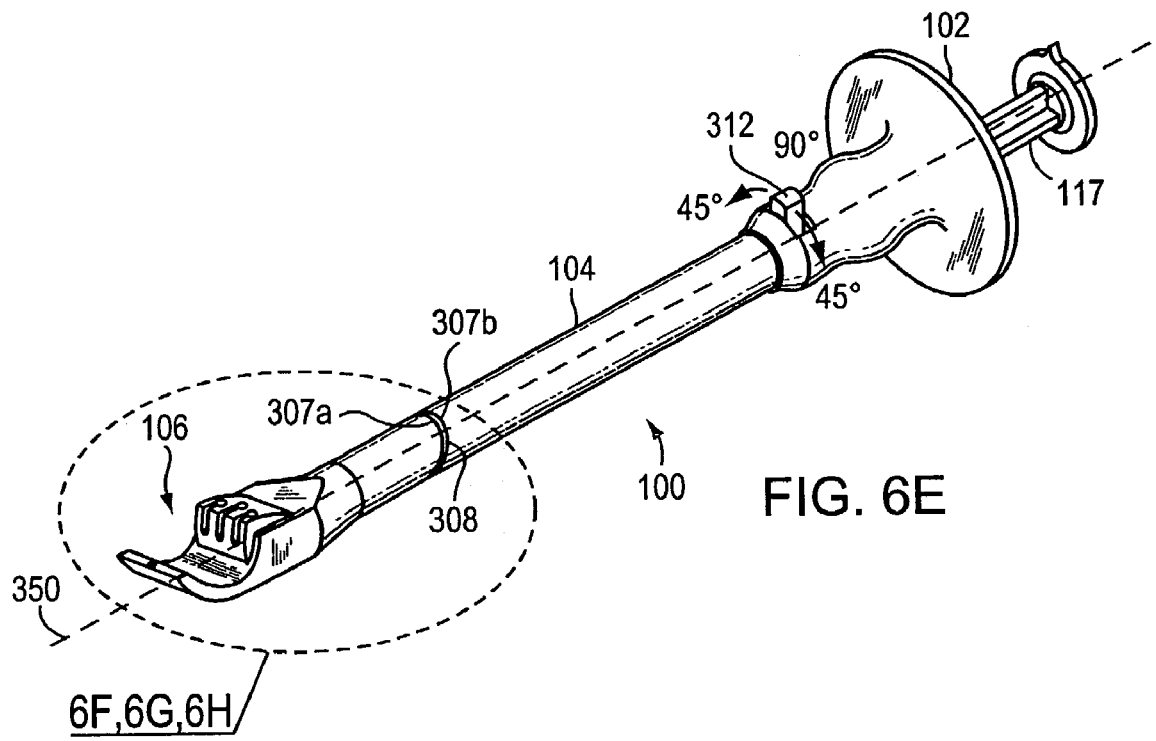
FIG. 6E is a schematic perspective view of an alternative embodiment of a suturing instrument having a deflectable distal portion.
Figures 6F, 6G, 6H:
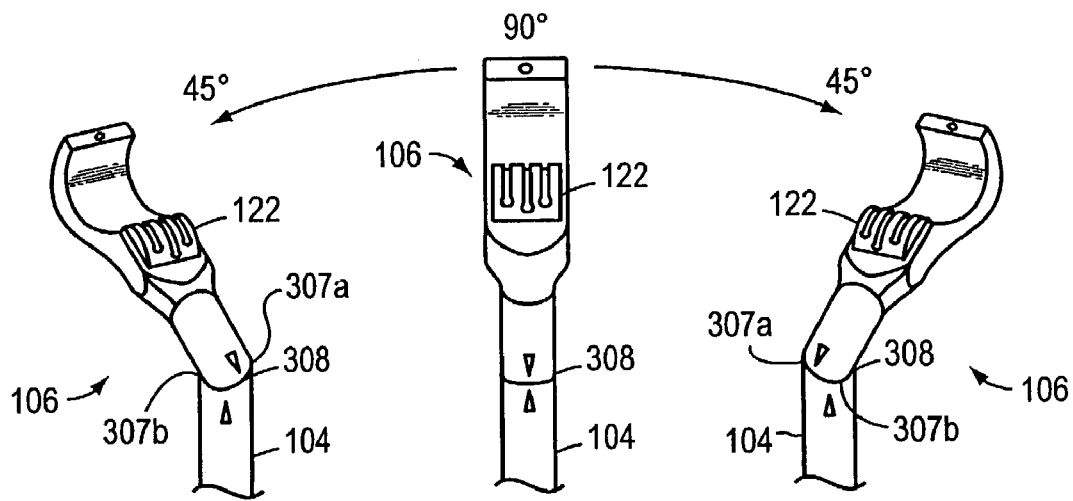
FIGS. 6F–6H are schematic perspective views of the deflectable distal portion of the suturing instrument of FIG. 6E in different positions.

Referring to FIGS. 6A and 6B, in another embodiment, the suturing instrument 100 includes a distal portion 106 that is independently deflectable and/or pivotable relative to the elongate member 104. Specifically, the distal portion 106 includes a deflectable portion 300 that connects the elongate body member 104 to the distal portion 106. The distal portion 106 is deflectable relative to the elongate member 104 in the "A-P" and "I-S" directions. Also, the operative portion 126 of the distal portion 106 may be pivotable about pivot nodes that define an axis 330 perpendicular to the longitudinal axis 350 of the elongate member 104. Alternatively, the operative portion 126 of the distal portion 106 may be pivotable about a pin 402 that is perpendicular to the longitudinal axis 350 of the elongate member 104 and defines the axis 330.

Referring to FIGS. 6C and 6D, movements of the distal portion 106 are controlled by one or more deflection control members 302, 306, and/or a pivot control lever 304 included in the proximal portion 108, for example, in the handle 102. The deflection control members 302 are coupled to a tension roller 315. The deflection control members 306 are coupled to a tension roller 311. Tension members 335 are connected to the tension rollers 311, 315, extend through the elongate member 104, and are coupled to a front portion 301*a* of a deflectable portion 300 for causing the distal portion 106 to deflect. The pivot control lever 304 is coupled to a pivot wire 334 that extends along the longitudinal axis 350 of the elongate member 104 and is coupled to the operative portion 126 of the distal portion 106 to cause it to pivot. The tension members 335 and the pivot wire 334 pass through a wire equalizer 313 disposed within the elongate body member 104 and are formed from, for example, stainless steel or Nitinol® alloy.

In operation, the user can pivot the operative portion 126 of the distal portion 106 about the axis 330 perpendicular to the longitudinal axis 350 of the elongate body member 104 by manipulating the pivot control lever 304 in the handle 102. The pivot control lever 304, when turned, causes the pivot wire 334 to pull or push the operative portion 126, thereby rotating it around the axis 330.

The deflection control members 302, 306 cause the tension rollers 311, 315 to turn when the deflection control members 302, 306 are turned, thereby causing the distal portion 106 to bend. Specifically, the user can bend the deflectable portion 300 of the distal portion 106 at its rear portion 301*b* up to +/−90 degrees (A-P direction) by manipulating the deflection control member 302, that causes the tension roller 315 to rotate and either tighten the tension member 335*a* and relax the tension member 335*p*, or tighten the tension member 335*p* and relax the tension member 335*a*. The user can also bend the deflectable portion 300 at its rear portion 301*b* up to +/−90 degrees (I-S direction) by manipulating the deflection control member 306, that causes the tension roller 311 to rotate and either tighten the tension member 335*i* and relax the tension member 335*s*, or tighten the tension member 335*s* and relax the tension member 335*i*.

Referring to FIGS. 6E–6H, in another embodiment, the suturing instrument 100 includes a distal portion 106 having a beveled surface 307*a* for contacting the elongate body member 104 and the elongate body member includes a beveled surface 307*b* for contacting the distal portion. According to one feature of this embodiment, the acute angle defined by the beveled surface 307*a* and the acute angle defined the beveled surface 307*b* are substantially equal. In one embodiment, each of these angles substantially equals 45 degrees. The surfaces 307*a*, 307*b* are secured against each other by a spring 310 disposed in the elongate member 104. In an aligned position, the surfaces 307*a*, 307*b* are aligned such that the distal portion 106 and the elongate body member 104 combine to produce a shaft that is substantially linear. The handle 102 includes a deflection control lever or member 312 that is coupled to a first end of a rod 320 that extends through the elongate member 104. A second end of the rod 320 is coupled to the distal portion 106. When the user manipulates the deflection control lever 312, the distal portion 106 rotates and, by virtue of the contacting beveled surfaces 307*a*, 307*b*, a rotation point 308 forms, thereby enabling suturing of tissue at any angle relative to the elongate body member's longitudinal axis 350 (or angles of surface contact).

In the embodiment shown in FIG. 6J, the suturing device 100 includes a locking mechanism that includes a ball 314 and a plurality of detents 316. The ball 314 is coupled to the beveled surface 307*b* of the elongate member 104 at a point radially outward from the longitudinal axis 350 of the distal portion 106. The ball 314 is positioned on the elongate member 104 to allow it to contact the beveled surface 307*a* of the distal portion 106. Each of the plurality of detents 316 may be disposed equally about the circumference about the beveled surface 307*a* of the distal portion 106. The circle of detents 314 may be centered on the longitudinal axis of the distal portion 106. Each detent 316 may have a radial distance from the longitudinal axis of the distal portion 106 equal to that of the ball 314. As the user deflects the distal portion 106 by manipulating the deflection control lever 312, the ball 314 moves out of one detent 316 and into another detent 316. The detents are spaced such that the distal portion rotates in a stepwise manner. Each step may be a fixed number of degrees of rotation. In another embodiment, the ball 314 is coupled to a spring 318 disposed in an aperture 321 formed in the beveled surface 307*b*. The spring 318 provides enough force to keep the ball 314 socketed in one of the detents when the user is not trying to change the angle of the distal portion 106 relative to the longitudinal axis 350 of the elongate body member 104. The spring 318 is, however, compressible such that the ball 314 is at least partially withdrawn into the aperture 321 and the user can easily change the angle of the distal portion 106 relative to the longitudinal axis 350 of the elongate body member 104 by moving the ball 314 from one detent 316*a* to another detent 316*b*.

In another embodiment, shown in FIG. 6K, the distal portion 106 and the elongate member 104 may include meshed teeth 319*a*, 319*b* that engage to lock the distal portion 106 and the elongate member 104 at a particular angle. In operation, the user pushes the distal portion 106 distally from the elongate member 104, so the beveled surfaces 307*a*, 307*b* do not contact each other and the teeth 319*a*, 319*b* no longer engage, and then deflects the distal portion 106 to a desired angle. Then, when the beveled surfaces 307*a*, 307*b* are brought into contact with each other, the teeth 319*a*, 319*b* engage or mesh to lock the distal portion 106 in place.

Figure 7A:
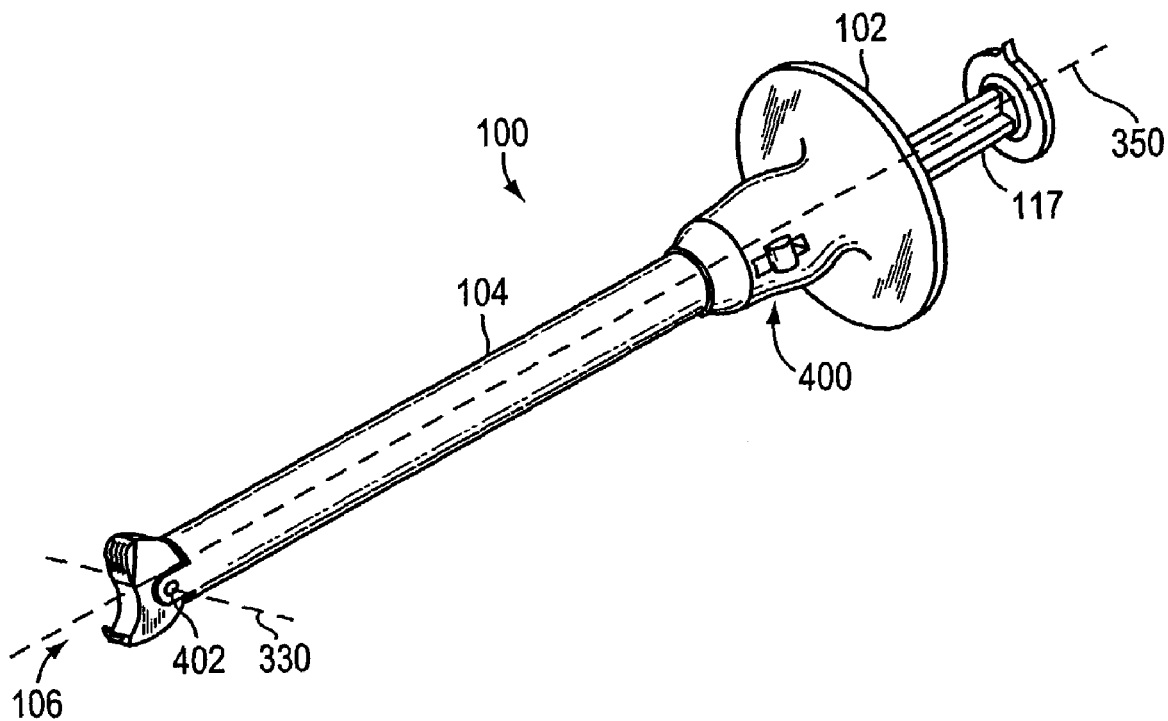
FIG. 7A is a schematic perspective view of a suturing instrument having a distal portion that is pivotable about one axis in accordance with the invention.
Figure 7B:
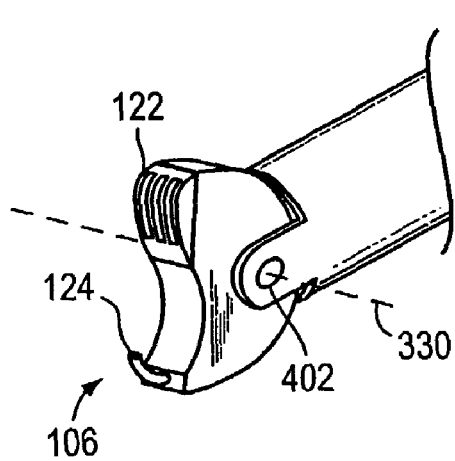
FIGS. 7B and 7C are enlarged schematic perspective views of the pivotable distal portion of the suturing instrument of FIG. 7A.
Figure 7C:
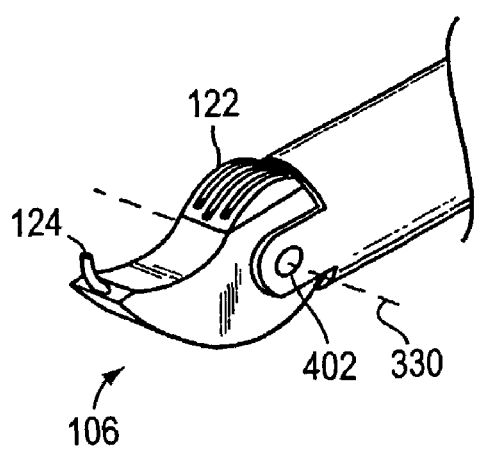
Figure 7G:
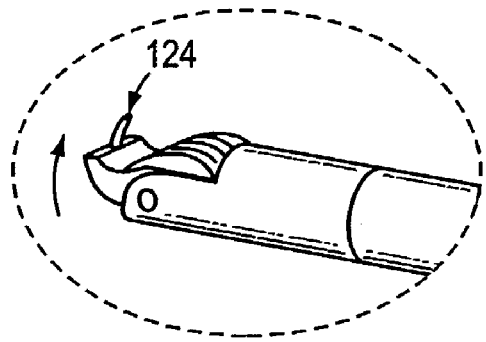
FIGS. 7E–7H are enlarged schematic perspective views of the distal portion of the suturing instrument of FIG. 7D.
Figure 7H:
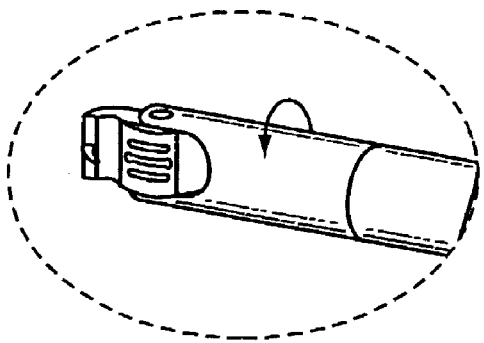
Figure 7D:
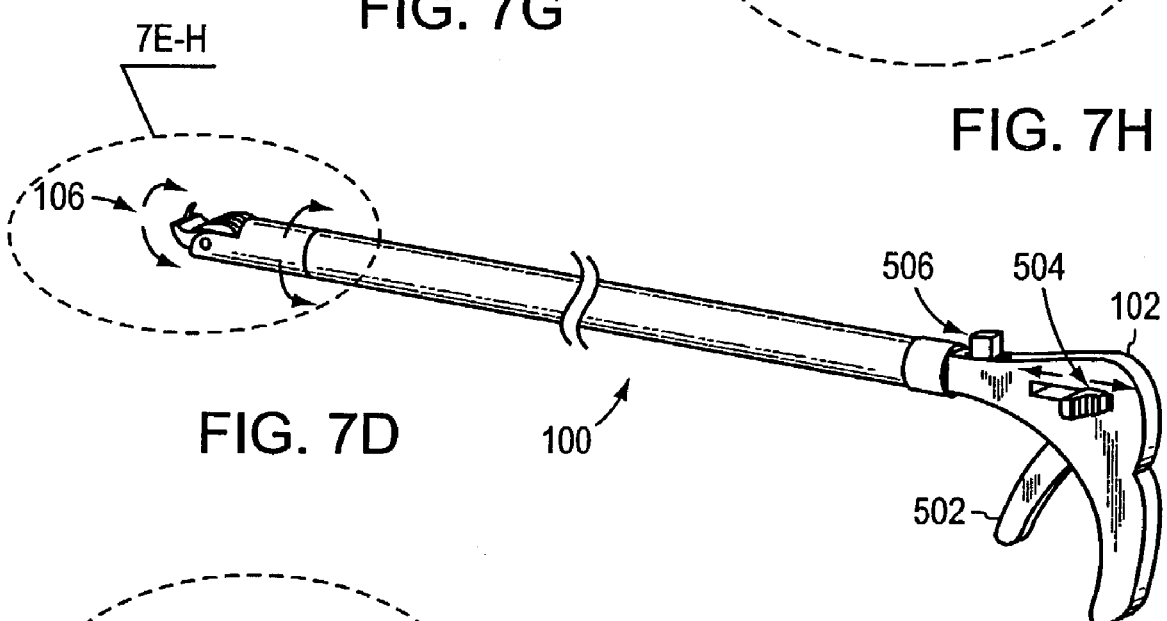
FIG. 7D is a schematic perspective view of a suturing instrument including a distal portion that is pivotable about two axes in accordance with the invention.
Figure 7E:
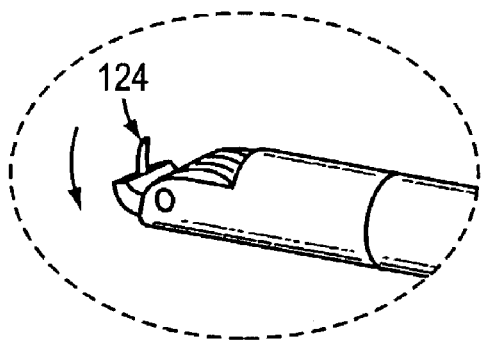
Figure 7F:
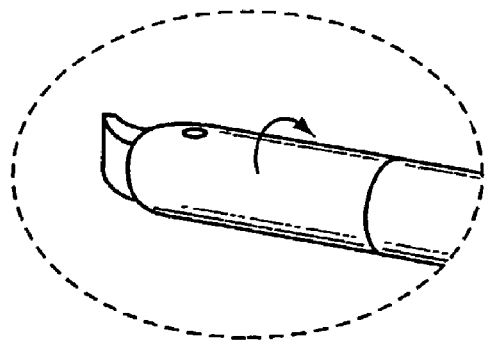

Referring to FIGS. 7A–7C, in another embodiment, the suturing instrument 100 includes a distal portion 106 that is independently pivotable about the axis 330 perpendicular to the longitudinal axis 350 of the elongate member 104 and rotatable about the longitudinal axis 350 of the elongate member 104. In one version of this embodiment, the degree of pivot is controlled by a pivot control lever 400 located on the handle 102 and coupled to a pivot control mechanism disposed within the elongate member 104. The pivot control mechanism is coupled to the distal portion 106. When the user manipulates the pivot control lever 400 slidably moving the pivot control mechanism within the elongate member 104, the distal portion 106 pivots about the pivot axis 330. This embodiment enables the suturing of tissue at angles up to 90 degrees from the longitudinal axis 350 of the elongate body member 104. The suturing instrument 100 also allows for removal from a 10 mm trocar without repositioning the distal portion 106.

Referring to FIGS. 7D–7H, in an alternative embodiment, the suturing instrument 100 includes a pivoting and rotating distal portion 106. The suturing instrument 100 also includes a pivot control lever 504, a rotation control lever 506, and a needle deployment trigger 502. The user can pivot the distal portion 106 by manipulating the pivot control lever 504 on the handle 102. The distal end 106 can be pivoted to a position perpendicular to the tissue plane to be sutured. The internal operation of the pivoting mechanism is similar to embodiments discussed above. The user can also rotate the distal portion 106 by manipulating the rotation control lever 506 also disposed on the handle 102, that is coupled to a rotation mechanism, which, in turn, is coupled to the distal portion 106. The needle 128 is deployed by pulling the needle deployment trigger 502. The needle deployment mechanism operates similar to other embodiments previously described.

Figure 8A:
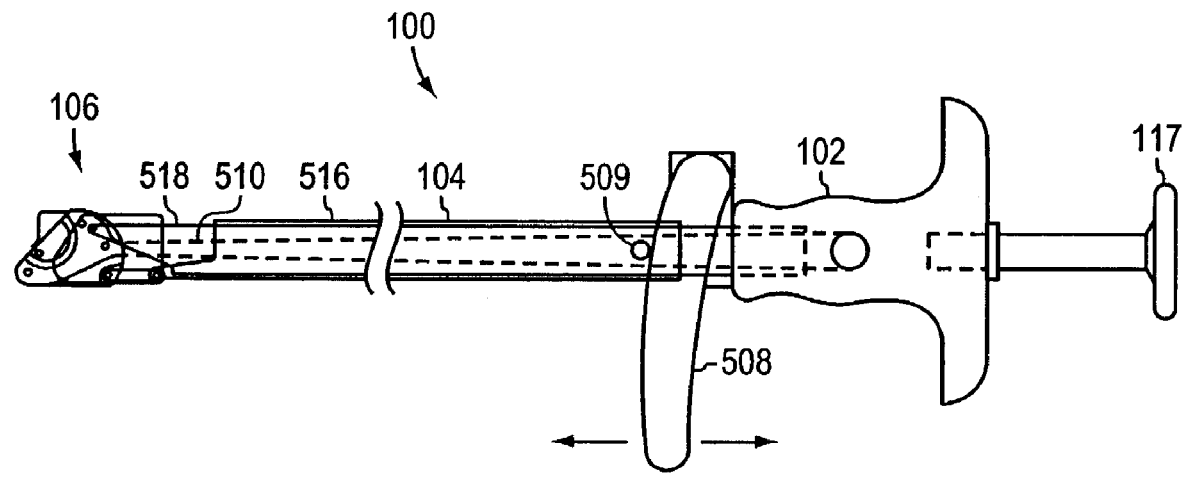
FIGS. 8A–8C are schematic plan views of a suturing instrument including an alternative embodiment of a pivotable distal portion in accordance with the invention.
Figure 8C:
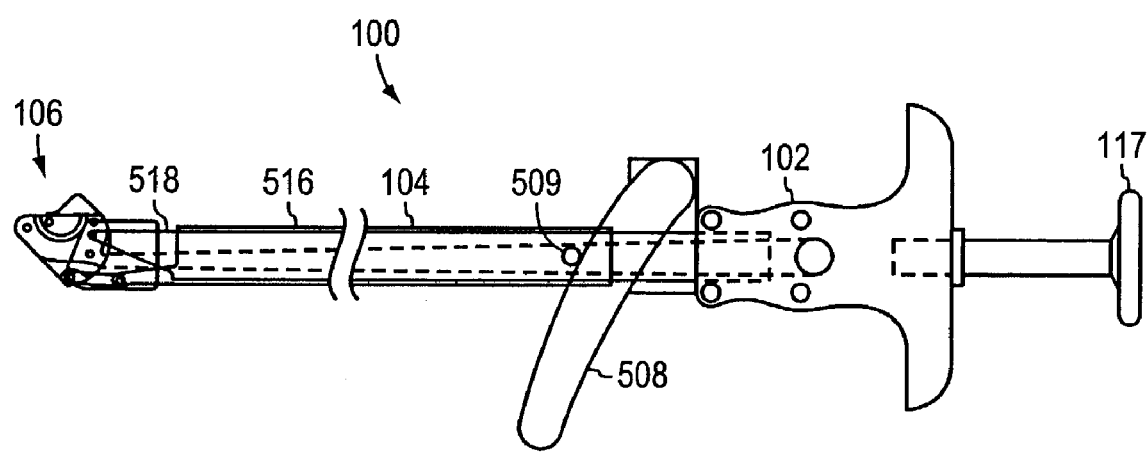
Figure 8B:
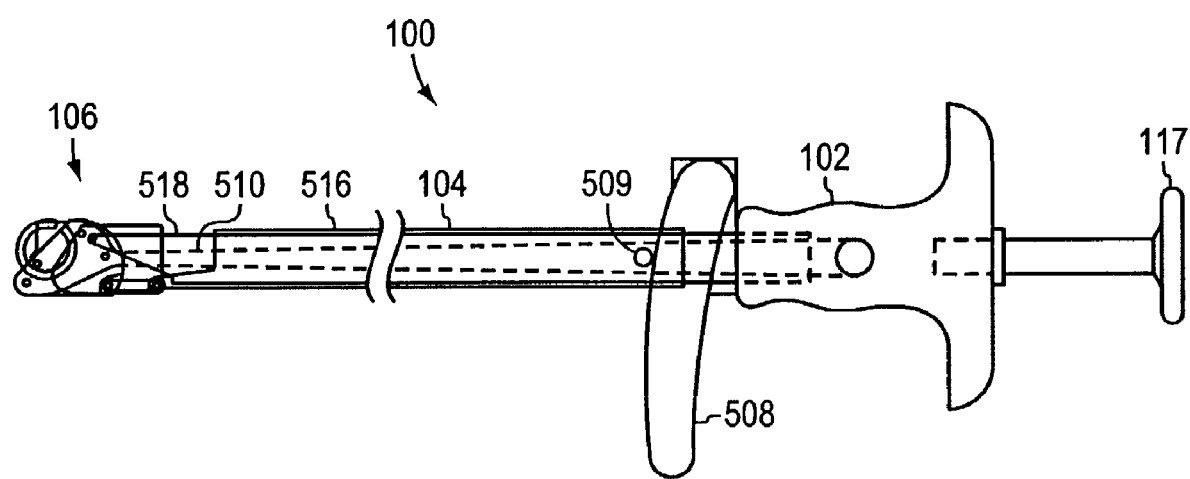
Figure 8D:
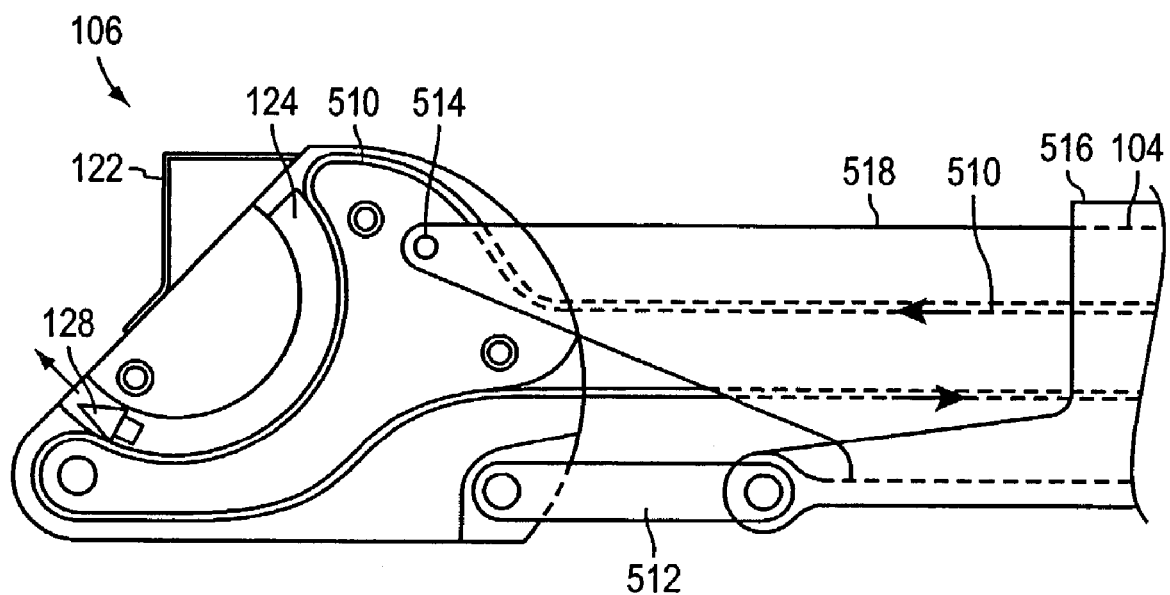
FIG. 8D is an enlarged schematic view of the distal portion of the suturing instrument of FIG. 8A.
Figure 8E:
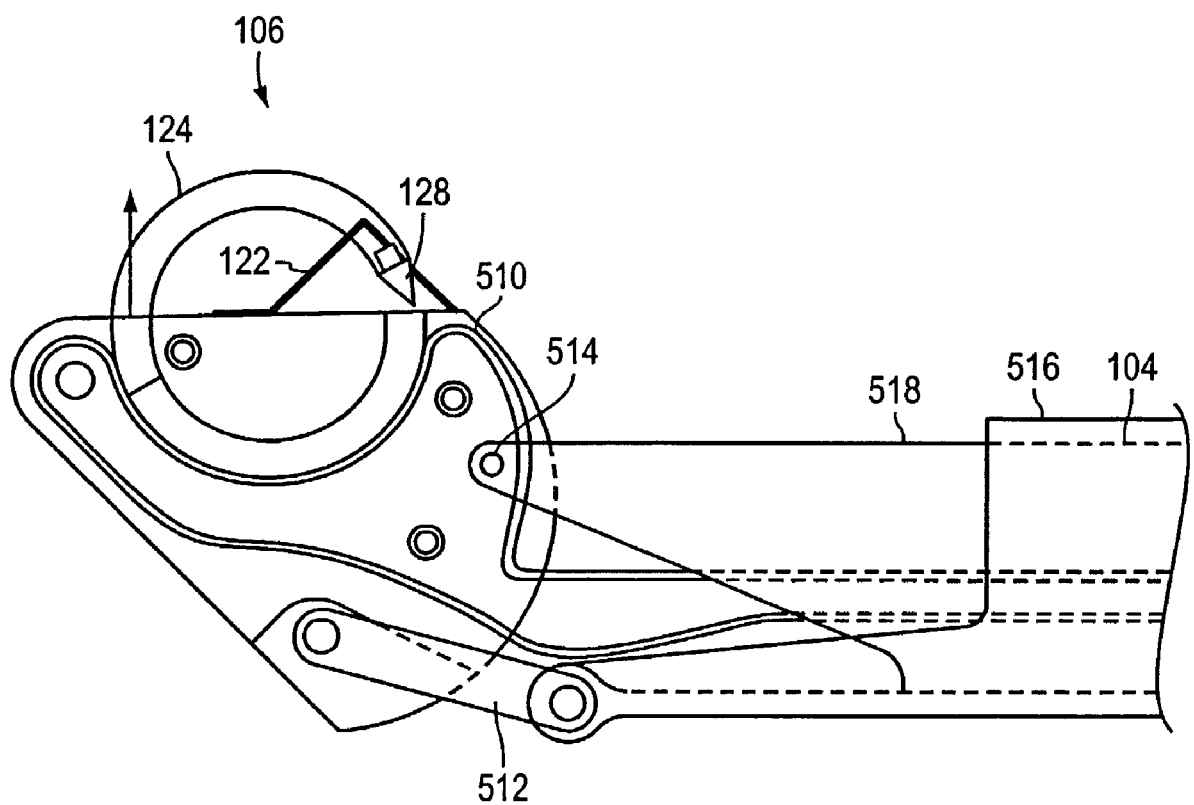
FIG. 8E is an enlarged schematic cross-sectional view of the distal portion of the suturing instrument of FIG. 8C.

Referring to FIGS. 8A–8E, in another embodiment, the suturing instrument 100 includes a pivoting distal portion 106 and a pivot control lever 508. The elongate member 104 includes an outer portion 516 and an inner portion 518, and is coupled to the distal portion 106 at a pivot point 514 and via linkage 512 (FIG. 8D). The user controls the pivoting action by manipulating the pivot control lever 508, thereby causing the outer portion 516 to slide relative to the inner portion 518. Pushing the control lever 508 causes the outer portion 516 to push the linkage 512, which, in turn, pushes the distal portion 106. As the distal portion 106 is pushed by the linkage 512, the distal portion pivots about the pivot point 514. The distal portion 106 can pivot up to 90 degrees relative to the longitudinal axis 350 of the elongate body member 104. Pulling the control lever 508 causes the outer portion 516 to pull the linkage 512, which pulls the distal portion 106. As the distal portion 106 is pulled by the linkage 512, the distal portion 106 pivots about the pivot point 514 and returns to its original position. In one embodiment, the control lever 508 maybe be coupled to the outer portion 516 via a pin 509 or other attachment means. Alternatively, the control lever 508 is not coupled to the outer portion 516, but is pushed into contact with the outer portion 516 via, for example, the pin 509. Further, the outer portion 516 may be biased against the control lever 508 by a spring that causes the distal portion 106 to return to its starting position when the control lever 508 is released.

According to this embodiment of the invention, in one version, the needle deployment mechanism 110 includes a loop 510 for advancing the needle carrier 124. The loop 510 is formed from a resilient material, such as rubber. The loop 510 is coupled to the button 117 at the proximal end of the elongate member 104 and coupled to the needle carrier 124 at a distal end. In operation, the user presses the button 117, which causes the loop 510 to advance. As the loop 510 advances, the needle carrier 124, which is coupled to the loop 510, also advances until the needle 128 in the needle carrier 124 is captured by the needle catch 122. After the needle 128 is captured in the needle catch 122, the user releases the button 117 and the loop 510 retracts thereby causing the needle carrier 124 to also retract.

Figure 9A:
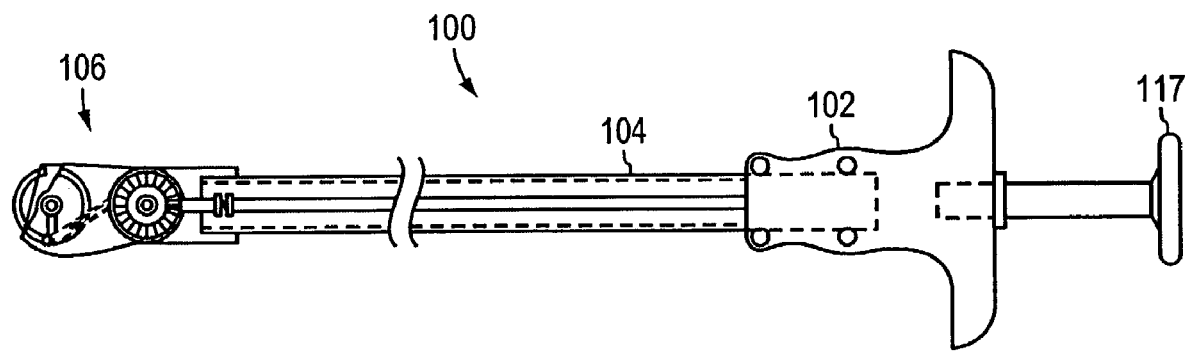
FIG. 9A is a schematic plan view of a suturing instrument including an alternative embodiment of a pivotable distal portion of a suturing instrument in accordance with the invention.
Figure 9B:
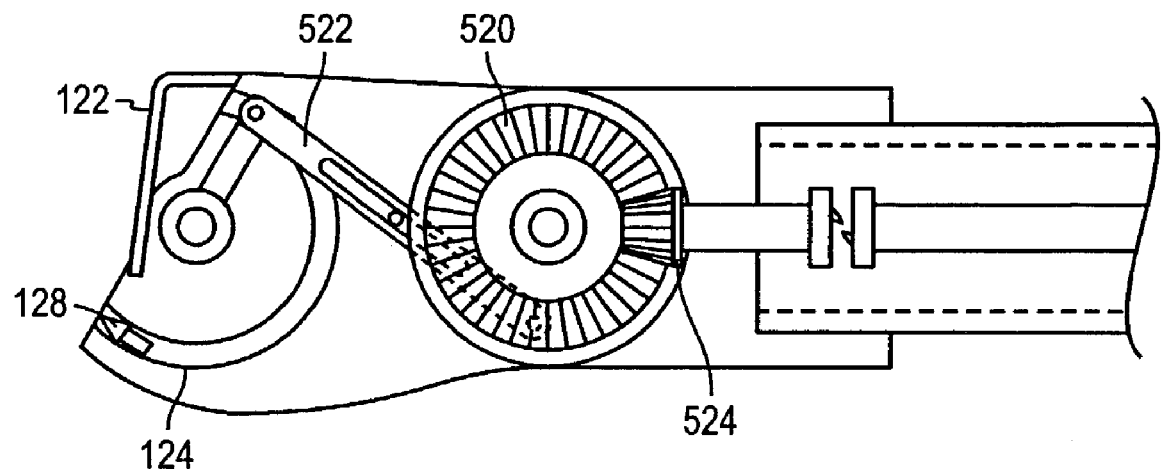
FIG. 9B is an enlarged schematic partial cross-sectional view of the distal portion of the suturing instrument of FIG. 9A.
Figure 9C:
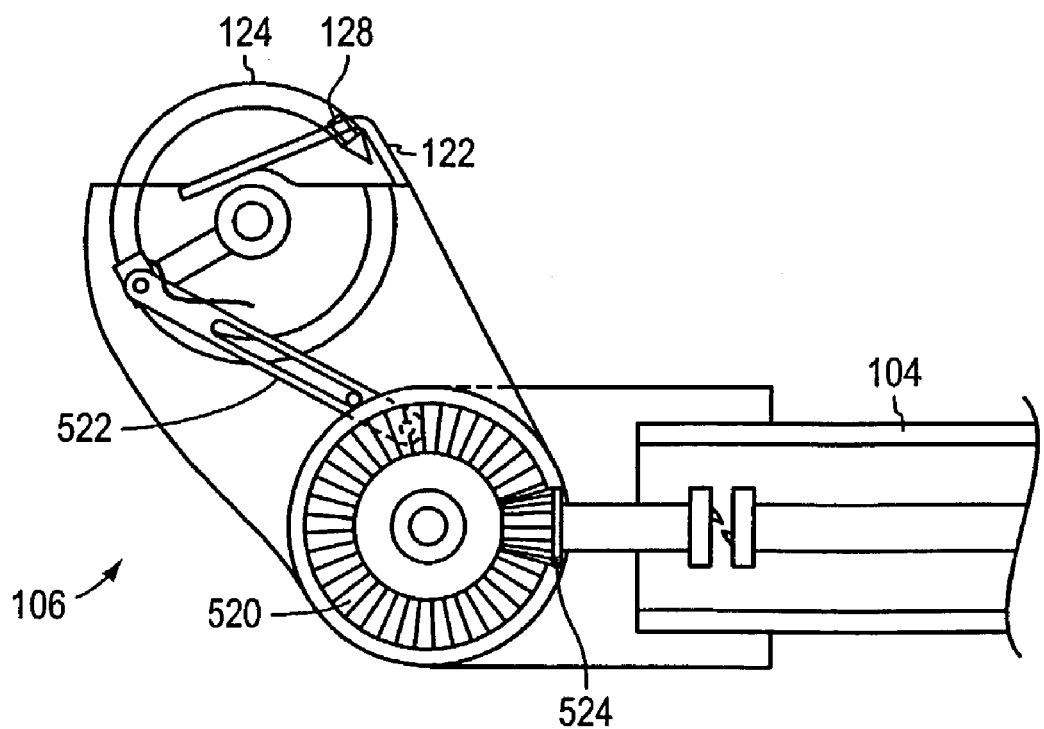
FIG. 9C is an enlarged schematic partial cross-sectional view of the distal portion of the suturing instrument of FIG. 9A in a pivoted position.

Referring to FIGS. 9A–9C, in another version of this embodiment, the needle deployment mechanism 110 in the distal portion 106 includes a first gear 520, a second gear 524, and a linkage 522. The linkage 522 is coupled to the first gear 520 and the needle carrier 124. In operation, the user manipulates the button 117, which causes the second gear 524 to turn. The second gear 524 engages the first gear 520, thereby causing the first gear 520 to turn and pivot the distal portion 106. As the first gear 520 turns, the linkage 522 moves and advances the needle carrier 124 until the needle 128 is captured by the needle catch 122. After the needle 128 is captured by the needle catch 122, the user releases the button 117 and the first gear 524 and the second gear 520 turn in the opposite direction causing the linkage 522 to retract the needle carrier 124.

Figure 10A:
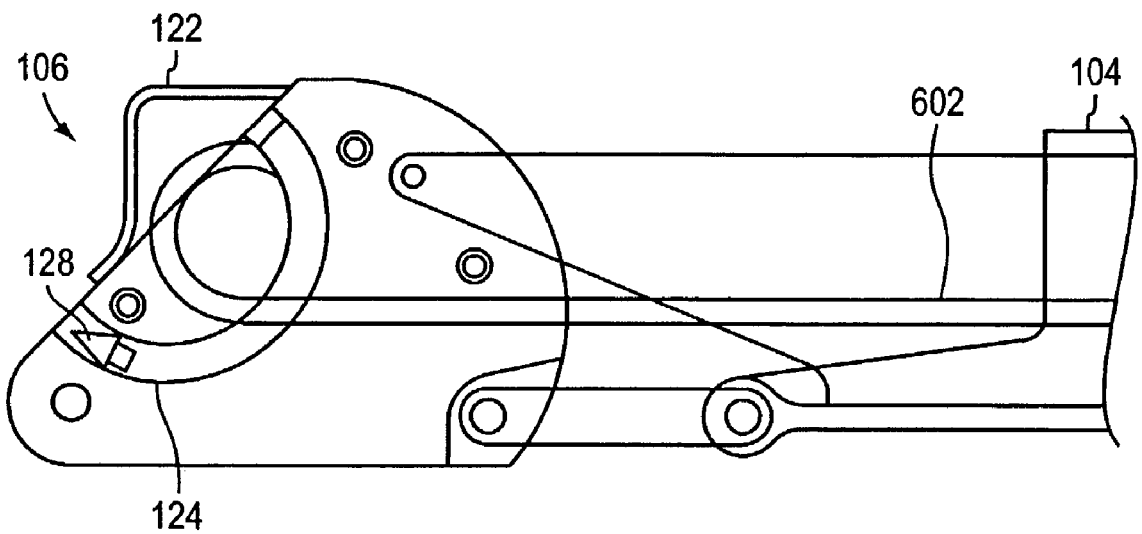
FIG. 10A is a schematic cross-sectional view of an alternative embodiment of a pivotable distal portion of a suturing instrument in accordance with the invention.
Figure 10B:
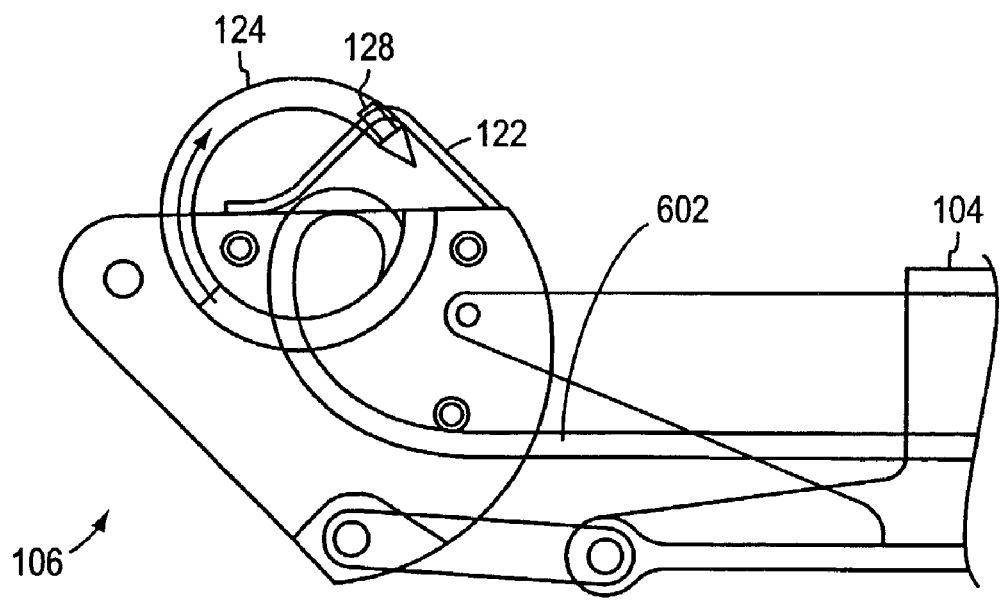
FIG. 10B is a schematic cross-sectional view of the pivotable distal portion of FIG. 10A in a pivoted position.

Referring to FIGS. 10A and 10B, in yet another embodiment, the needle deployment mechanism in the distal portion 106 includes a superelastic pusher 602. A proximal end of the superelastic pusher 602 is coupled to the button 117 (shown in FIG. 1B) and a distal end of the superelastic pusher 602 is coupled to the needle carrier 124. In operation, the user pushes the button 117, which causes the superelastic pusher 602 to advance the needle carrier 124 until the needle 128 is captured in the needle catch 122. After the needle 128 is captured by the needle catch 122, the user releases the button 117 and the superelastic pusher 602 retracts the needle carrier 124. This embodiment operates similarly to the embodiment described with reference to FIGS. 1A–1C. The superelastic pusher can be formed from an elastic material having "superelastic" properties, such as Nitinol®.

Figure 11A:
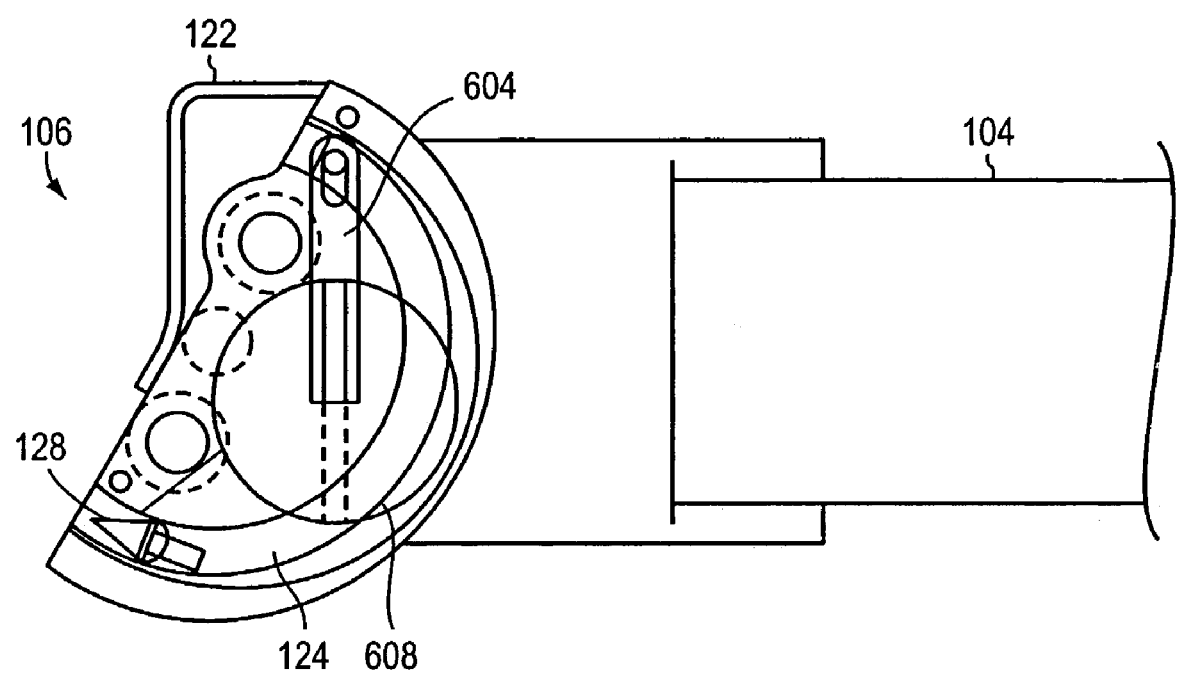
FIG. 11A is a schematic cross-sectional view of an alternative embodiment of a pivotable distal portion of a suturing instrument including a drum-and-camshaft needle deployment mechanism in accordance with the invention.
Figure 11B:
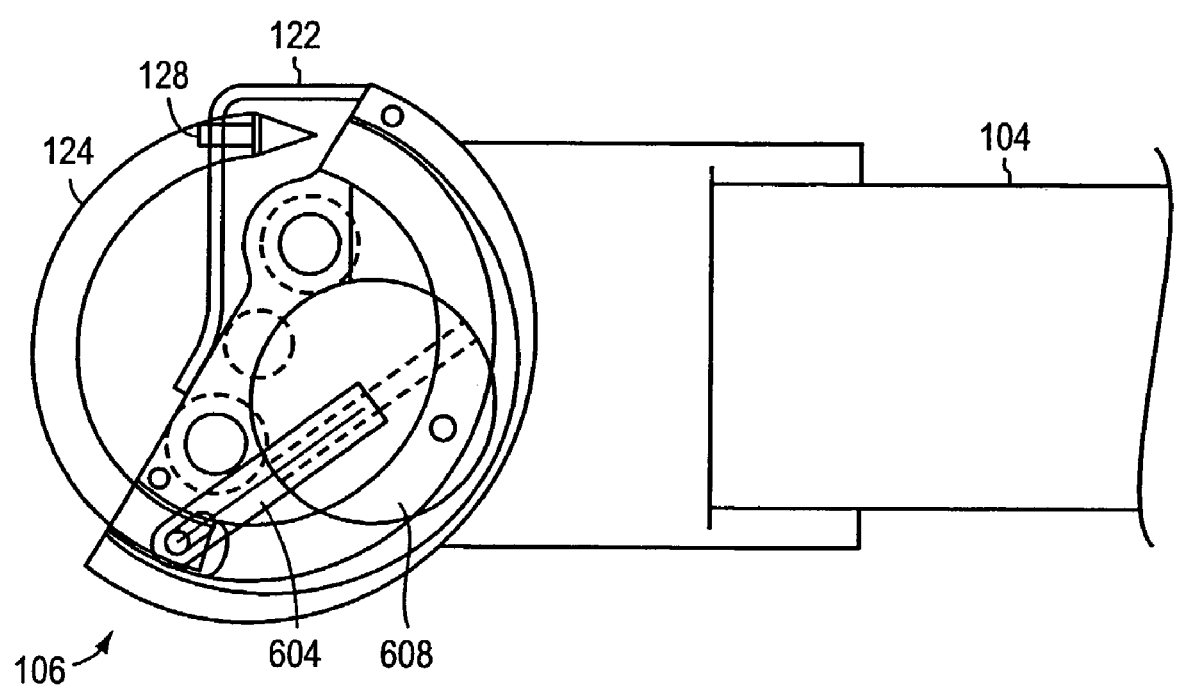
FIG. 11B is a schematic cross-sectional view of the distal portion of the suturing instrument of FIG. 11A with a needle deployment mechanism in a deployed position.

Referring to FIGS. 11A and 11B, in another embodiment, the needle deployment mechanism in the distal portion 106 includes a drum 608 and a camshaft 604. The drum 608 is coupled to a distal end of a push wire. A proximal end of the push wire is coupled to the button 117. The drum 608 is also coupled to the camshaft 604 and the camshaft 604 is coupled to the needle carrier 124. In operation, the user pushes the button 117, which causes the push wire to rotate the drum 608. As the drum 608 rotates, the camshaft 604 moves and advances the needle carrier 124 until the needle 128 is captured in the needle catch 122. After the needle 128 is captured by the needle catch 122, the user releases the button 117 and the push wire rotates the drum 608 in the opposite direction, thereby causing the camshaft 604 to retract the needle carrier 124. The push wire can be formed from, for example, stainless steel or nickel-titanium alloy.

Referring to FIGS. 12A–12C, in still another embodiment, the suturing instrument 100 is configured to be used with an endoscope 708. A proximal portion 712 of the suturing instrument 100 includes the handle 102, a carrier drive wire socket 702 attached to a distal end 752 of the handle 102, and an actuator 112 including a needle deployment button 117. The proximal portion 712 also includes a scope adapter 706 having a distal end 718 that is connectable to an access port 724 of the endoscope 708 and a proximal end 720 that is connectable to the carrier drive wire socket 702.

The suturing instrument further includes an elongate member 714 that includes a carrier drive wire 710, which can be formed from, for example, stainless steel or a nickel-titanium alloy, covered by a flexible sheath 704. The sheath 704 is coupled to a distal portion 716. The carrier drive wire 710 is connectable to the needle carrier for moving a needle from the distal portion in accordance with any of the embodiments disclosed herein. Also, the distal portion 716 can be stationary, pivoting, or rotatable in accordance with any of the embodiments disclosed herein.

In operation, the elongate member 714 is fed into a distal end 722, through a working channel 726, and out of an access port 724 of the endoscope 708. The distal end 718 of the adapter 706 is coupled to the access port 724 of the endoscope 708 and the carrier drive wire 710 is fed through the adapter 706. The carrier drive wire 710 is then coupled the carrier drive wire socket 702 and the proximal portion 712 of the suturing instrument 100 is secured to the proximal end 720 of the adapter 706. The endoscope 708 can then be inserted into a patient. The adapter 706 can include any standard or custom fittings necessary to couple to the access port 724 and the proximal portion 712 of the suturing instrument 100. For example, the adapter 706 can include a luer fitting or a treaded fitting to couple to the endoscope 708.

In one embodiment, the sheath 704 is fixedly coupled to the distal portion 716, and the distal portion 716 can be rotated by rotating the flexible sheath 704, using, for example, a rotation controller 760 disposed in the scope adapter 706. In another embodiment, the handle 102 of the suturing instrument 100 includes two subassemblies. The subassemblies include a thumb-button/finger grasper assembly and a thumb-button/scope assembly.

Other embodiments incorporating the concepts disclosed herein may be used without departing from the spirit and scope of the invention. The described embodiments are to be considered in all respects as only illustrative and not restrictive. Therefore, it is intended that the scope of the invention be only limited by the following claims.

What is claimed is:

1. A suturing instrument comprising:
   an elongate body member comprising a middle portion and a distal portion extending distally from the middle portion, the distal portion being pivotable about an axis, and deflectable in a plurality of directions relative to the middle portion; and
   a needle deployment mechanism disposed at least partially within the elongate body member and connectable to a needle for moving the needle out of the distal portion,
   wherein the distal portion comprises a first beveled surface for contacting the middle portion, the first beveled surface defining a first angle, and wherein the middle portion comprises a second beveled surface for contacting the distal portion, the second beveled surface defining a second angle and being formed with an aperture,
   wherein the elongate body member further comprises:
      a plurality of detents defined by the first beveled surface and circumferentially disposed about the first beveled surface;
      a ball disposed in the second beveled surface and dimensioned to fit at least one of the plurality of detents;
      a first resilient member for biasing the distal portion towards the middle portion along a longitudinal axis of the elongate member; and
      a second resilient member disposed in the aperture for biasing the ball into engagement with the at least one of the plurality of detents.

2. The suturing instrument of claim 1 wherein the first angle substantially equals the second angle.

3. The suturing instrument of claim 2 wherein the sum of the first angle and the second angle substantially equals 90 degrees.

4. The suturing instrument of claim 1 wherein the elongate body member further comprises a deflection control mechanism disposed at least partially therein and coupled to the distal portion for deflecting the distal portion at the predetermined angle relative to the middle portion by rotating the distal portion about a longitudinal axis of the elongate body member.

5. A suturing instrument comprising:
   an elongate body member comprising a middle portion and a distal portion extending distally from the middle portion and deflectable at a predetermined angle relative to the middle portion; and
   a needle deployment mechanism disposed at least partially within the elongate body member and connectable to a needle for moving the needle out of the distal portion,
   wherein the distal portion comprises a first beveled surface for contacting the middle portion, the first beveled surface defining a first angle, and wherein the middle portion comprises a second beveled surface for contacting the distal portion, the second beveled surface defining a second angle and being formed with an aperture,
   and wherein the elongate body member further comprises;
      a plurality of detents defined by the first beveled surface and circumferentially disposed about the first beveled surface;
      a ball disposed in the second beveled surface and dimensioned to fit at least one of the plurality of detents;
      a first resilient member for biasing the distal portion towards the middle portion along a longitudinal axis of the elongate member;
      a second resilient member disposed in the aperture for biasing the ball into engagement with the at least one of the plurality of detents; and
      a deflection control mechanism disposed at least partially therein and coupled to the distal portion for deflecting the distal portion at the predetermined angle relative to the middle portion by rotating the distal portion about a longitudinal axis of the elongate body member.

6. A suturing instrument comprising:
   an elongate body member comprising a middle portion and a distal portion extending distally from the middle portion and deflectable at a predetermined angle relative to the middle portion; and
   a needle deployment mechanism disposed at least partially within the elongate body member and connectable to a needle for moving the needle out of the distal portion,
   wherein the distal portion comprises a first beveled surface for contacting the middle portion, the first beveled surface defining a first angle, and wherein tho middle portion comprises a second beveled surface for contacting the distal portion, the second beveled surface defining a second angle,
   wherein the elongate body member further comprises a locking mechanism for securing the distal portion at the predetermined angle relative to the middle portion, wherein the locking mechanism comprises
      a plurality of detents defined by the first beveled surface and circumferentially disposed about the first beveled surface; and
      a ball disposed in the second beveled surface and dimensioned to fit at least one of the plurality of detents,
   wherein the second beveled surface defines an aperture for receiving the ball therein, further comprising a second resilient member disposed in the aperture for biasing the ball into engagement with the at least one of the plurality of detents.

* * * * *